United States Patent [19]

Wellinghoff et al.

[11] Patent Number: 5,705,092
[45] Date of Patent: Jan. 6, 1998

[54] MULTILAYERED BIOCIDAL FILM COMPOSITIONS

[75] Inventors: Stephen T. Wellinghoff; Joel J. Kampa, both of San Antonio, Tex.

[73] Assignee: Southwest Research Institute, San Antonio, Tex.

[21] Appl. No.: 461,304

[22] Filed: Jun. 5, 1995

[51] Int. Cl.$^6$ .................. A01N 25/08; A01N 25/34
[52] U.S. Cl. .................. 252/187.21; 252/187.23; 424/410; 424/412
[58] Field of Search .................. 252/186.01, 186.33, 252/186.36, 186.21, 186.24, 187.23; 424/412, 410

[56] References Cited

U.S. PATENT DOCUMENTS

| | | | |
|---|---|---|---|
| 2,071,625 | 2/1937 | Haas et al. | 99/172 |
| 2,482,891 | 9/1949 | Aston | 252/187 |
| 2,546,568 | 3/1951 | Taylor | 99/150 |
| 2,558,942 | 7/1951 | Eagleson | 167/30 |
| 3,183,057 | 5/1965 | Marks et al. | 21/58 |
| 3,585,147 | 6/1971 | Gordon | 252/187 |
| 3,591,515 | 7/1971 | Lovely | 252/187 |
| 3,767,787 | 10/1973 | Segal | 424/76 |
| 4,104,190 | 8/1978 | Hartshorn | 252/187 R |
| 4,330,531 | 5/1982 | Alliger | 424/149 |
| 4,499,077 | 2/1985 | Stockel et al. | 424/149 |
| 4,504,442 | 3/1985 | Rosenblatt et al. | 422/37 |
| 4,547,381 | 10/1985 | Mason et al. | 426/316 |
| 4,585,482 | 4/1986 | Tice et al. | 106/15.05 |
| 4,681,739 | 7/1987 | Rosenblatt et al. | 422/37 |
| 4,689,169 | 8/1987 | Mason et al. | 252/186.24 |
| 4,728,498 | 3/1988 | Theeuwes | 422/29 |
| 4,748,904 | 6/1988 | Razeto et al. | 99/467 |
| 4,829,129 | 5/1989 | Kelley | 525/326.9 |
| 4,880,638 | 11/1989 | Gordon | 424/662 |
| 4,889,654 | 12/1989 | Mason et al. | 252/100 |
| 4,891,216 | 1/1990 | Kross et al. | 424/78 |
| 4,925,645 | 5/1990 | Mason | 423/477 |
| 4,956,184 | 9/1990 | Kross | 424/661 |
| 4,975,109 | 12/1990 | Friedman, Jr. et al. | 71/67 |
| 4,986,990 | 1/1991 | Davidson et al. | 424/665 |
| 5,126,070 | 6/1992 | Leifheit et al. | 252/186.36 |
| 5,252,343 | 10/1993 | Kross | 424/661 |
| 5,306,440 | 4/1994 | Ripley et al. | 252/186.33 |
| 5,360,609 | 11/1994 | Wellinghoff | 514/772.3 |
| 5,384,134 | 1/1995 | Kross et al. | 424/661 |
| 5,387,350 | 2/1995 | Mason | 210/754 |
| 5,399,288 | 3/1995 | Marzouk et al. | 252/186.21 |
| 5,405,549 | 4/1995 | Pitochelli | 252/187.21 |
| 5,631,300 | 5/1997 | Wellinghoff | 514/772.3 |

FOREIGN PATENT DOCUMENTS

| | | |
|---|---|---|
| 1048200 | 1/1991 | China . |
| 0 287 074 | 4/1988 | European Pat. Off. . |
| 0 611 162 | 2/1994 | European Pat. Off. . |
| 0 611 163 | 2/1994 | European Pat. Off. . |
| 57-198775 | 12/1982 | Japan . |
| 60-092759 | 5/1985 | Japan . |
| 04/164005 | 6/1992 | Japan . |
| 6-107971 | 4/1994 | Japan . |
| 2151138 | 12/1984 | United Kingdom . |
| WO 85/04107 | 3/1985 | WIPO . |
| WO 88/09176 | 5/1988 | WIPO . |
| WO 96/18300 | 6/1996 | WIPO . |

OTHER PUBLICATIONS

Caplus 1994: 598552, 1994.
Caplus 1991: 250229, 1991.

*Primary Examiner*—Shean C. Wu
*Attorney, Agent, or Firm*—Senniger, Powers, Leavitt & Roedel

[57] ABSTRACT

A multilayered composite for providing sustained release of chlorine dioxide includes a hydrophobic layer containing an acid releasing agent, and a hydrophilic layer containing chlorite anions. The hydrophilic and hydrophobic layers are adjacent and substantially free of water, and the hydrophilic layer is capable of releasing chlorine dioxide upon hydrolysis of the acid releasing agent.

50 Claims, 11 Drawing Sheets

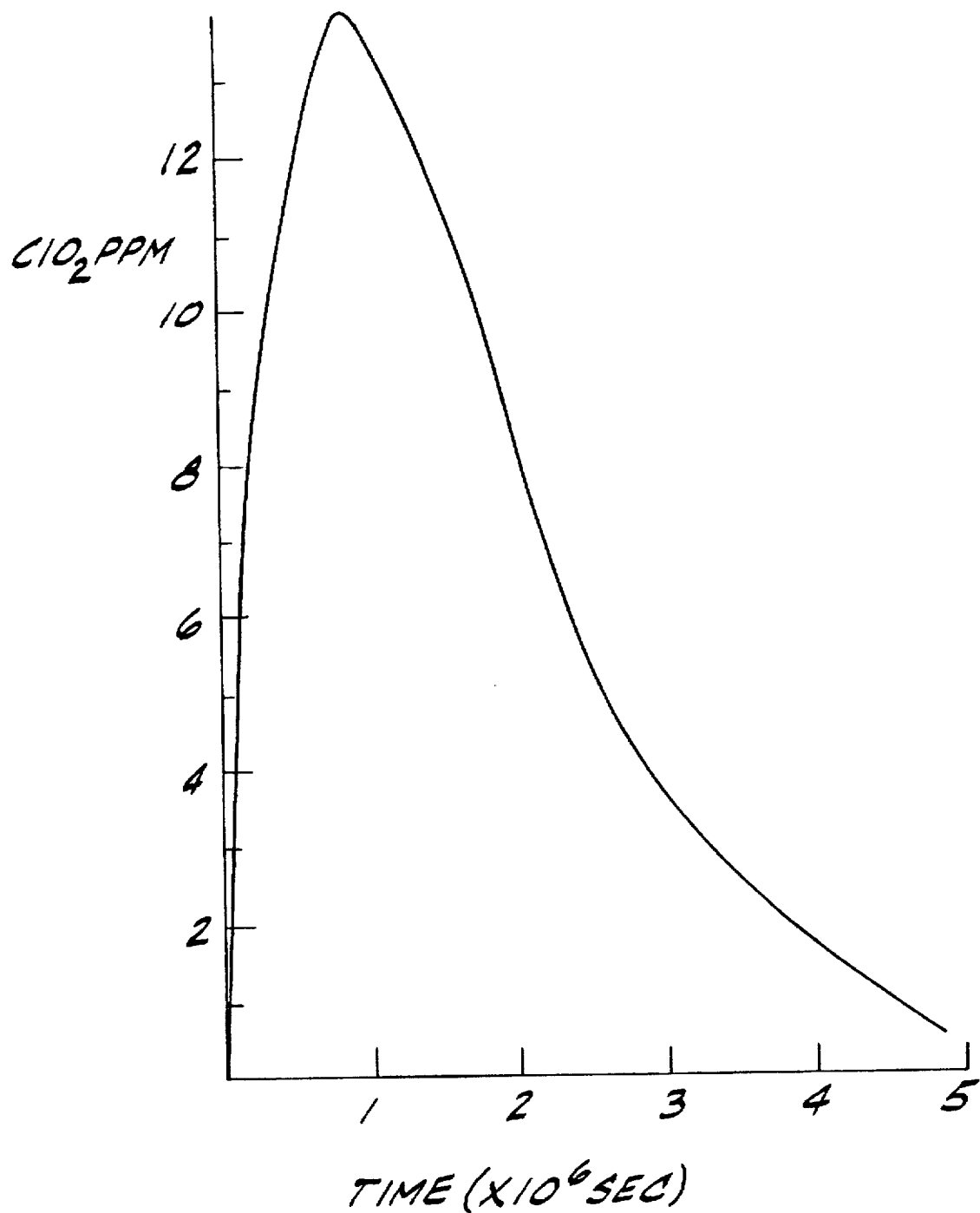

MULTILAYERED BIOCIDAL FILM COMPOSITIONS

BACKGROUND OF THE INVENTION

The present invention relates generally to a biocidal composition that releases chlorine dioxide. The invention particularly relates to a composite including separate hydrophobic and hydrophilic layers which form a chlorine dioxide releasing film when in contact.

Chlorine dioxide ($ClO_2$) is a superior oxidizing agent widely used as a bleach, disinfectant, fumigant or deodorizer. It can penetrate the cell wall or membrane and cytoplasm of mold spores, bacteria and other microbiological contaminants at concentrations below one part per million and destroy them.

The incorporation of chlorine dioxide or sodium chlorite in food packaging has prompted studies to determine whether residual levels of such preservatives result in a significant genetic or carcinogenic hazard to humans. Meier et al. studied the effect of subchronic and acute oral administration of chlorine, chlorine dioxide, sodium chlorite and sodium chlorate on the induction of chromosomal aberrations and spermhead abnormalities in mice [Environ. Mutagenesis, 7, 201 (1985)]. Only the highly reactive hypochlorite resulted in a weak positive effect for mutagenic potential. The other compounds, including chlorine dioxide and sodium chlorite, failed to induce any chromosomal aberrations or increased numbers of micronuclei in the bone marrow of mice. Vilagines et al. attribute the relatively innocuous effect of chlorine dioxide to its inability to produce halomethanes, unlike hypochlorite and chlorine [Proc. AWWA Disinfect. Semin., 24 pp. (1977); Chem. Abs. 93, 173513f]. Recently, Richardson et al. reported that an extensive study of the reaction of chlorine dioxide with water borne organics by the Environmental Protection Agency confirmed this observation [Environ. Sci. Technol., 28, 592 (1994)].

Japanese Kokai Nos. 63/296,758, 63/274,434, and 57/168,977 describe deodorants containing chlorine dioxide incorporated in a polymer, ceramic beads, or calcium silicate wrapped in nonwoven cloth, respectively. Gels that generate chlorine dioxide for use as topical applications for disinfection are disclosed by Kenyon et al., Am. J. Vet. Res., 45(5), 1101 (1986). Chlorine dioxide generating gels are generally formed by mixing a gel containing suspended sodium chlorite with a gel containing lactic acid immediately prior to use to avoid premature chlorine dioxide release. Chlorine dioxide releasing gels have also been used in food preservation.

Encapsulation processes have also been used in preparing sources of chlorine dioxide. Canadian Patent No. 959,238 describes generation of chlorine dioxide by separately encapsulating sodium chlorite and lactic acid in polyvinyl alcohol and mixing the capsules with water to produce chlorine dioxide.

Tice et al., U.S. Pat. No. 4,585,482 describe gradual hydrolysis of alternating poly(vinyl methyl ether-maleic anhydride) or poly(lactic-glycolic acid) to generate acid which can release chlorine dioxide from sodium chlorite. A polyalcohol humectant and water are encapsulated with the polyanhydride or polyacid in a nylon coating. After sodium chlorite is diffused into the capsule through the nylon wall, an impermeable polystyrene layer is coacervated around the nylon capsule. Solvents are required for reaction and application of the capsules. The capsules can be coated onto surfaces to release chlorine dioxide. Although the capsules are said to provide biocidal action for several days to months, chlorine dioxide release begins immediately after the capsules are prepared. The batchwise process used to prepare the capsules also involves numerous chemical reactions and physical processes, some of which involve environmental disposal problems.

There is a need for a composite that can be easily activated to initiate chlorine dioxide release in use. A composite that generates only FDA approved substances is particularly needed for food packaging and other applications where the substances can be ingested by or in contact with humans.

SUMMARY OF THE INVENTION

Among the objects of the invention, therefore, may be noted the provision of a composite that releases a concentration of chlorine dioxide sufficient to eliminate bacteria, fungi, molds and viruses; the provision of such a composite that releases such chlorine dioxide concentrations for a period of up to several months; the provision of such a composite that can be stored for a prolonged period and then activated prior to use; the provision of such a composite that increases the release rate of chlorine dioxide in proportion to increased temperature and humidity that promotes mold and bacteria growth; and the provision of such a composite that only releases substances approved for human exposure or ingestion and is relatively inexpensive.

The present invention is directed to a multilayered composite for providing sustained release of chlorine dioxide includes a hydrophobic layer containing an acid releasing agent, and a hydrophilic layer containing chlorite anions. The hydrophilic and hydrophobic layers are adjacent and substantially free of water, and the hydrophilic layer is capable of releasing chlorine dioxide upon hydrolysis of the acid releasing agent.

Another embodiment of the present invention is directed to a multilayered composite for providing sustained release of chlorine dioxide that includes a layer having a hydrophobic phase containing an acid releasing agent and a hydrophilic phase containing chlorite anions, the hydrophilic and hydrophobic phases being interdispersed and substantially free of water. A moisture regulating layer is in contact with a surface of the layer, such that moisture permeating the moisture regulating layer hydrolyzes the acid releasing agent to initiate release of chlorine dioxide from the multilayered composite.

Another embodiment of the invention is a multilayered composite for providing time pulsed release of chlorine dioxide including at least one hydrophobic layer containing an acid releasing agent, at least one hydrophilic layer containing chlorite anions, and at least three barrier layers to control the diffusion of water into the hydrophobic layer or the diffusion of hydronium ions produced by hydrolysis of the acid releasing agent into the hydrophilic layer. The arrangement of the layers in the composite is defined by the formula $C(ACB)_nC$ wherein C is a barrier layer, A is a hydrophobic layer, B is a hydrophilic layer, and n is an integer ranging from 1 to 10.

Other objects and advantages of the invention will be apparent from the following detailed description.

BRIEF DESCRIPTION OF THE DRAWINGS

FIG. 11 is a plot of chlorine dioxide concentration as a function of time.

DETAILED DESCRIPTION OF THE PREFERRED EMBODIMENT

Figure 1:
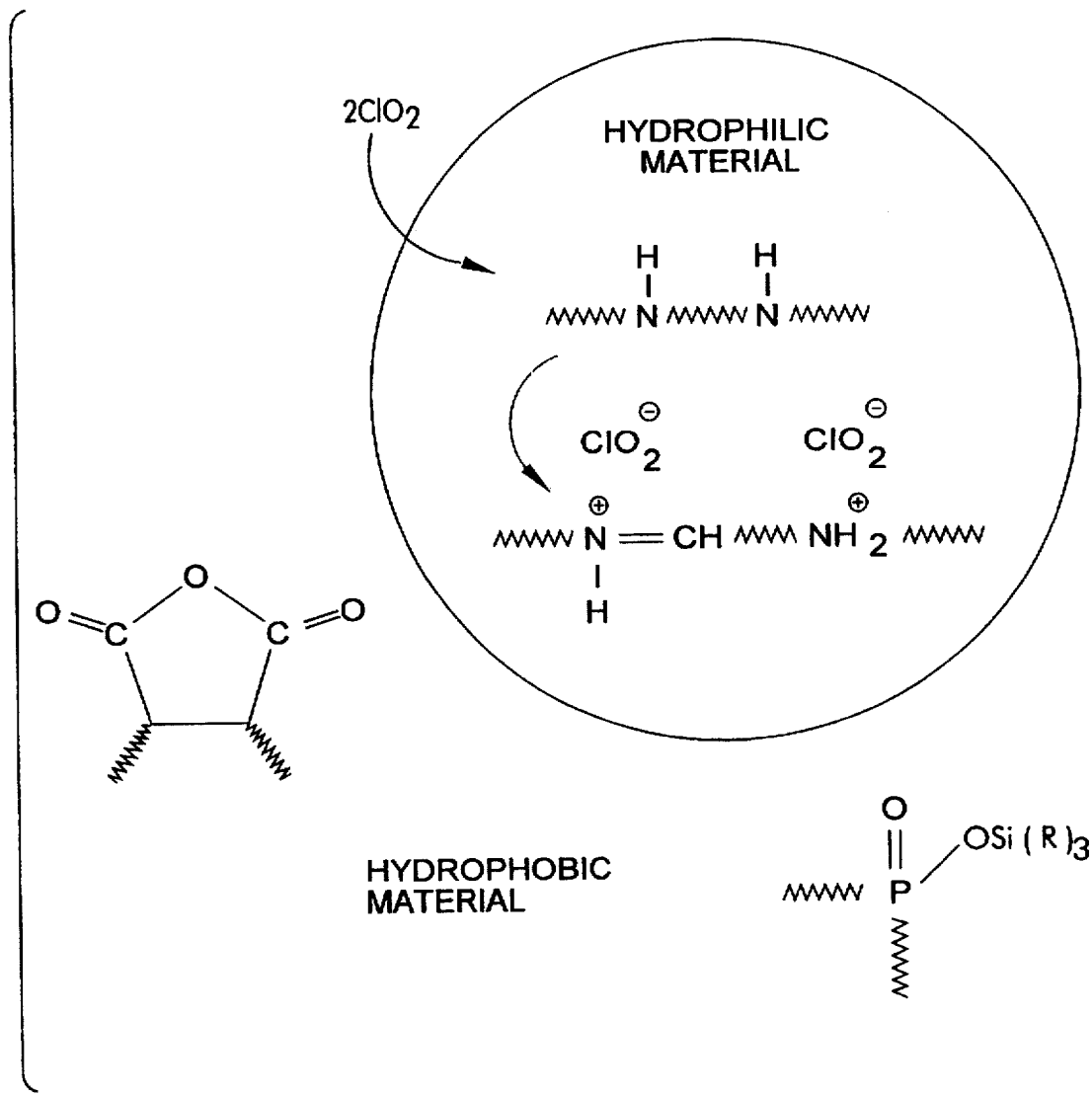
FIG. 1 is a schematic that illustrates conversion of an amine precursor to an iminium chlorite.

In accordance with the present invention, it has been discovered that sustained release of chlorine dioxide can be generated from a composite containing chlorite anions when the composite is exposed to moisture. The composite comprises a hydrophilic material and a hydrophobic material. The composite may be, for example, a dispersion composed of hydrophilic and hydrophobic phases, or a mechanical combination of the hydrophilic and hydrophobic materials, such as powders and adjacent films. The powder has a hydrophobic core embedded with chlorite containing particles. Adjacent films comprise separate layers of the hydrophilic or hydrophobic materials.

Generally, the composite comprises between about 5.0 wt. % and about 95 wt. % hydrophilic material and between about 5.0 wt. % and about 95 wt. % hydrophobic material, preferably between about 15 wt. % and about 95 wt. % hydrophilic material and between about 15 wt. % and about 95 wt. % hydrophobic material. If the composite is a dispersion, either material can form the continuous phase. The continuous phase constitutes between about 15 wt. % and about 95 wt. % of the dispersion and the dispersed phase constitutes between about 5 wt. % and about 85 wt. % of the dispersion, and preferably, the continuous phase constitutes between about 50 wt. % and about 95 wt. % of the dispersion and the dispersed phase constitutes between about 5 wt. % and about 50 wt. % of the dispersion.

The hydrophobic material of the composite can be composed entirely of an acid releasing agent or can comprise the acid releasing agent in combination with a diluent and/or a plasticizer. Any acid releasing agent that is capable of being hydrolyzed by ambient moisture is acceptable for purposes of the present invention. Preferably, the acid releasing agent does not react with the hydrophilic material, and does not exude or extract into the environment. The hydrophobic material comprises between about 10 wt. % and about 100 wt. % of the acid releasing agent, up to about 80 wt. % diluent, and up to about 60 wt. % plasticizer, and preferably, between about 40 wt. % and about 100 wt. % of the acid releasing agent, between about 20 wt. % and about 80 wt. % diluent, and up to about 20 wt. % plasticizer.

The hydrophilic material of the composite can be composed entirely of a source of chlorite anions or can comprise the chlorite anion source in combination with another hydrophilic material. The hydrophilic material can contain an amine, amide or an alcohol, or a compound containing amino, amido or hydroxyl moieties and having a high hydrogen bonding density. A source of chlorite anions is incorporated in the hydrophilic material and can constitute between about 2 wt. % and about 40 wt. % of the hydrophilic material in the form of chlorite anions and counterions, and preferably, between about 8 wt. % and about 10 wt. % of the hydrophilic material. When the chlorite source is a chlorite salt, the salt dissociates in the hydrophilic material such that the hydrophilic material in the composite will include chlorite anions and counterions. However if the hydrophilic material is an amine and the chlorite source is chlorine dioxide gas, the chlorine dioxide reacts with the amine to form iminium chlorite in situ, if the oxidation potential of the amine is sufficiently low for the amine to be oxidized.

It has been found that the acid releasing agent within the hydrophobic material is hydrolyzed by adsorbed moisture, releasing acid and hydronium ions that diffuse from the hydrophobic material to the hydrophilic material containing chlorite anions. The hydronium ions react with the chlorite anions in the hydrophilic material, releasing chlorine dioxide gas that diffuses out of the composite into the surrounding atmosphere for a period of up to about six months in order to prevent the growth of bacteria, molds, fungi and viruses on a treated surface.

The hydrophobic and hydrophilic materials are substantially free of water to avoid significant release of chlorine dioxide prior to use of the composite. For purposes of the present invention, a hydrophilic material, a hydrophobic material, or a dispersion thereof is substantially free of water if the amount of water in the composite does not provide a pathway for transmission of hydronium ions from the hydrophobic material to the hydrophilic material. Generally, each of the hydrophilic and hydrophobic materials can include up to about 0.1 wt. % water without providing such a pathway for interdiffusion between the materials. Preferably, each material contains less than about $1.0\times10^{-3}$ wt. % water, and, more preferably, between about $1\times10^{-2}$ wt. % and about $1\times10^{-3}$ wt. % water. Insubstantial amounts of water can hydrolyze a portion of the acid releasing agent to produce acid and hydronium ions within the composite. The hydronium ions, however, do not diffuse into the hydrophilic material until enough free water is present for transport of hydronium ions.

The chlorite anions generally do not react with the hydrophilic material, but are surrounded by hydrogen bonds contributed by the nitrogen or hydroxide within the hydrophilic material. Suitable chlorite sources that can be incorporated into the composite of the present invention include alkali metal chlorites such as sodium chlorite or potassium chlorite, alkaline-earth metal chlorites such as calcium chlorite, or chlorite salts of a transition metal ion or a protonated primary, secondary, tertiary or quaternary amine. Many chlorite sources, such as sodium chlorite, are stable at processing temperatures in excess of about 100° C., allowing for processing at relatively high temperatures.

FIG. 1 illustrates preparation of a composite containing iminium chlorite. The amine hydrophilic material is in contact with a hydrophobic acid releasing agent (both hydrolyzed P—O—Si and maleic anhydride are shown in FIG. 1). Chlorine dioxide ($ClO_2$) is reduced by extracting an electron from the amine, forming an aminium radical cation (not shown) and a chlorite counterion ($ClO_2^-$). The aminium cation quickly converts to an iminium cation by loss of a proton from an adjacent carbon atom and oxidation by another chlorine dioxide molecule. The mechanism for above reaction in an aqueous system is described by Rosenbatt et al., J. Org. Chem., 28, 2790 (1963); J. Amer. Chem. Soc. 89(5), 1158, 1163 (1967).

High chlorine dioxide to chlorite conversions are obtained if the chlorite anion and/or iminium cation that is generated by the initial electron transfer from the amine are rapidly complexed and stabilized by a hydrophilic molecule. In some formulations, uncomplexed chlorite anion may be depleted by subsequent reactions with the iminium counterion at temperatures above about 60° C. Chlorites are also subject to disproportionation into chloride and chlorate. An amine with a high $pK_a$ is preferred because it reacts more rapidly with chlorine dioxide and acts as a more effective proton sink, maintaining the basic pH required for chlorite ion stability.

Figure 2:
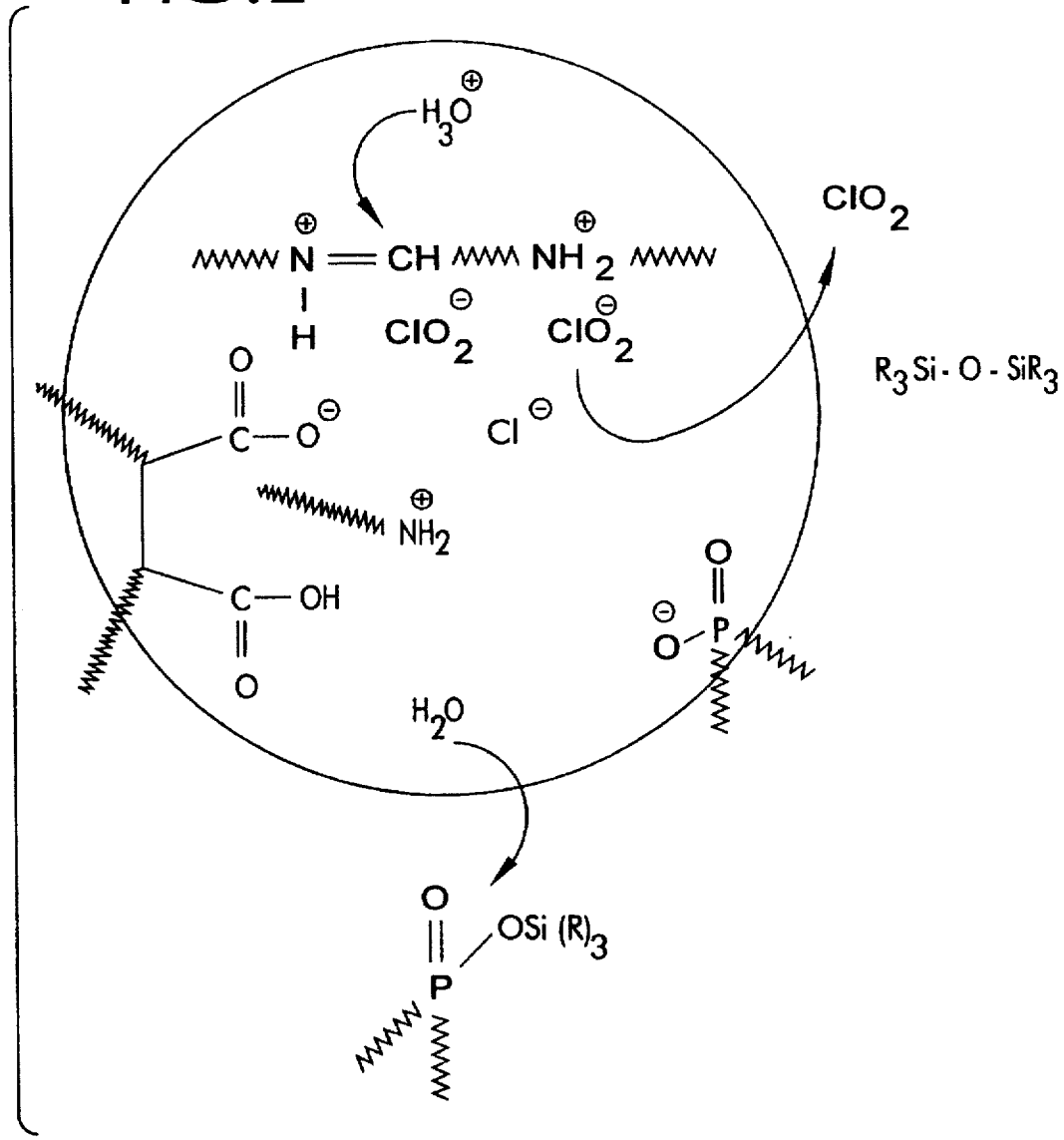
FIG. 2 illustrates hydrolysis of an acid anhydride in a hydrophobic phase and migration of hydronium ion to the iminium chlorite to release chlorine dioxide gas.

FIG. 2 illustrates the mechanism for release of chlorine dioxide from iminium chlorite when moisture contacts the composite. Hydrolysis of the acid releasing agent provides hydronium cations ($H_3O^+$) that react with iminium chlorite to release chlorine dioxide gas. The decomposition products of the reaction are an aminium cation (shown as

in FIG. 2), a carboxylate (COO—, not shown in FIG. 2), and Cl. These products are retained within the composite.

It has been found that, in some instances, iminium chlorite may decompose if the composite is exposed to temperatures exceeding about 60° C., reducing the available chlorite concentration for conversion to chlorine dioxide. In order to maximize chlorine dioxide release from the composite, it has been discovered that the chlorite source can be omitted from the composite until the composite is applied to a surface when the hydrophilic material in the composite is an amine. After application, the composite is exposed to chlorine dioxide gas that either reacts with the amine to form iminium chlorite in situ or dissolves in the amine to provide chlorite anions. The composite is then activated in the presence of moisture to release chlorine dioxide. This method enables the composite to be exposed to elevated temperatures during processing, storage and application as compared to the temperatures at which the iminium chlorite decomposes, because the hydrophilic material does not contain iminium chlorite or any chlorite anions. The method also precludes premature release of chlorine dioxide from the composite. Chlorine dioxide can be provided on site by passing the composite through a chlorine dioxide generator.

Conventional chlorine dioxide generators generate an atmosphere of chlorine dioxide that is saturated with water. Chlorine dioxide that comes into contact with the composite of the invention must first be dissolved into a material that does not absorb water such as a low melting hydrocarbon wax or chlorohydrocarbon wax. Alternatively, chlorine dioxide is dried with a desiccant. Chlorine dioxide is thus delivered from a wet industrial process into the composite without exposing the composite to water.

In order for an amine to form iminium chlorite in neat form or in the presence of a plasticizer, the amine must be sufficiently electron rich and the amine nitrogen must be locally mobile. Electron withdrawing groups should be separated from the amine center by at least two methylene groups in order for the chlorine dioxide to extract an electron from the amine. Movement of the bonds about the nitrogen center of the amine is required for aminium formation. If the amine is frozen into a glassy matrix, the amine nitrogen will not be mobile and the amine will not convert to iminium chlorite. A glassy amine can be softened to increase mobility by adding at least about 10 wt. % of a plasticizer, such as a low molecular weight amide, to the amine to lower glass transition temperature below the reaction temperature. Other suitable plasticizers are well known in the polymer art.

The rate of chlorine dioxide release from a composite can be altered by changing the viscosity of the hydrophilic and hydrophobic materials, changing the dispersibility of the hydrophilic and hydrophobic materials, changing the temperature of the composite, changing the concentration of acid releasing agent in the composite, adding a desiccant or humectant to the composite to control release of chlorine dioxide from the composite once it is exposed to moisture, or changing the volume fractions of the hydrophilic and hydrophobic materials to produce continuous or discrete phases within a dispersion.

Maximum chlorine dioxide release from a composite can also be achieved by stabilizing the chlorite anion. Iminium chlorite is unstable to nucleophilic attack by the chlorite anion. It has been discovered that the room temperature lifetime of chlorite anion is substantially extended when a strong base, such as a metal alkoxide, is present in the hydrophilic material containing the iminium chlorite. The mechanism of alkoxide stabilization of the chlorite counterion is shown below.

wherein $R'_2$ and $R_2$ are groups that correspond to those of the selected amine and R' is an alkyl or hydrogen group. In the absence of water, the iminium ion is immediately decomposed into an α-amino ether and a more stable sodium chlorite salt. If water is present during the oxidation of the tertiary amine, an unstable α-amino alcohol is formed that can attack the chlorite anion unless the chlorite anion has been effectively complexed by the hydrophilic solvent. Addition of water after solvation of the chlorite ion is not as deleterious.

Acceptable strong bases for use in stabilizing the chlorite include metal alkoxides such as sodium, potassium or calcium methoxides, ethoxides, propoxides or butoxides, metal oxides such as aluminum oxide, or sodium oxide, metal ions such as $Na^+$, trialkyl ammonium salts of alkoxides, ammonium salts of alkoxides, acetates such as sodium acetate, substituted acetates, or other materials that would generate a strong basic reaction to attack the nitrogen center of iminium chlorite.

In a hydrophilic material containing a tertiary amine (dimethylaminoacrylamide), N-methylacetamide and urea, an α-amino ether and chlorite salt is formed when the iminium chlorite is stabilized. Any monomeric or oligomeric amide substituted plasticizer, such as succinamide, formamide, or N-methyl formamide, can be substituted for N-methylacetamide in order to soften the amine. Formamide and N-methyl formamide are toxic and would not be preferred in applications involving human contact. If the amine center is sufficiently mobile, the addition of a plasticizer is unnecessary. Urea improves the chlorine dioxide uptake and releases efficiency of the hydrophilic material because it has a high hydrogen bonding density and will not react with the acid releasing agent. Compounds having a high amide concentration can also be used to improve hydrophilic material efficiency. Preferably, the composite comprises between about 5 wt. % and about 95 wt. % of the hydrophilic material and between about 5 wt. % and about 95 wt. % of the hydrophobic material. The hydrophilic material comprises between about 5 to about 30 wt. % of an amine and between about 70 and about 95 wt. % of a hydrophilic solvent including between about 35 and about 55 wt. % urea, between about 35 wt. % and about 55 wt. % plasticizer and about 10 wt. % base. It has been found that not more than about 0.5 moles of chlorine dioxide per mole of amine should be added to the hydrophilic material or the stability of the material could be compromised.

Preferred amides for use as the hydrophilic material include formamide, acrylamide-isopropylacrylamide, copolymers of formamide and acrylamide-isopropylacrylamide, and copolymers of acrylamide, isopropylacrylamide or N,N-methylene bisacrylamide and a primary amine or a secondary amine. Such amides can be useful vehicles for film casting prior to exposure to chlorine dioxide, which does not react with polymerizable, electron deficient alkenes such as acrylamide.

Suitable amines for use as the hydrophilic material include primary amines, secondary amines, and tertiary amines having pendant hydrogen bonding groups. An amine substituted with electron donating groups that donate electrons to convert chlorine dioxide to chlorite is preferred. Electron withdrawing groups concentrate electron density at such groups such that it is difficult for the chlorine dioxide to extract an electron from the amine. Tertiary amines having non-hydrogen bonding pendant groups that are dissolved in a hydrophilic solvent are also acceptable. Representative amines include: alkanolamines; copolymers of aminoalkanes and alkene bisacrylamides; alkylaminopyridine; alkene diamines; alkylamino cycloalkanes; alkylaminocarboxyamido alkanes dissolved in a diluent; amines having the formula $R_{3-x}NH_x$; $R_1R_2NCH_2CH_2c(O)NH_2$; solubilized $N(CH2CH_2OH)_{3-x}H_x$, $lR_5R_6N(CH_2)_xNHC(O)NH_2$ $N(CH_2CH_2NHC(O)NH_2)_3$, $[R_4—CH_2—CH_2—\overset{O}{\overset{\|}{C}}—NH\frac{1}{2}CH_2$, or $+NH—(CH_2)_nNH—CH_2CH_2\overset{O}{\overset{\|}{C}}—NHCH_2NH\overset{O}{\overset{\|}{C}}CH_2CH_2\}_m$;

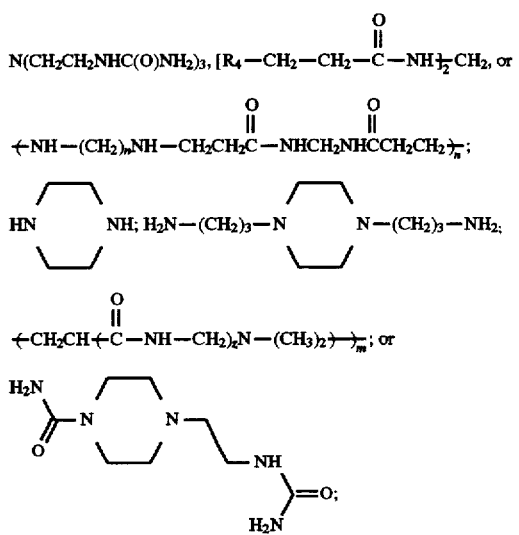

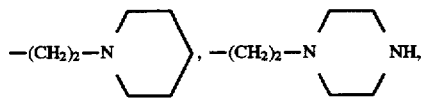

wherein: R substituents are, independently, —$(CH_2CH_2O)_y$ H, $C(CH_3)_2(CH_2)_zOH$, —$(CH_2)_zNH$ $(CH_2CH_2O)_zH$, —CH $(CH_3)_2$, alkyl, cycloalkyl, benzyl, acrylamide, or pyridyl; $R_1$, $R_2$, $R_5$, and $R_6$ are alkyl; $R_3$ is straight chain $C_6$ to $C_{12}$ alkyl; $R_4$ is cycloalkyl or benzyl; m is 1–100; n is 2 or 3; x is 0, 1 or 2; y is 1 or 2; and z is 1–6. Generally, the above compounds can be solubilized in formamide, isopropylacrylamide-acrylamide or other conventional plasticizers.

Preferred amines include monoethanolamine, diethanolamine, triethanolamine, a copolymer of 1,3-diaminopropane or 1,2-diaminoethane and N,N-methylene bisacrylamide, 4-dimethylaminopyridine, tetramethylene ethylene diamine, N,N-dimethylamino cyclohexane, solubilized 1-(N-dipropylamino)-2-carboxyamido ethane or 1-(N-dimethylamino)-2-carboxyamido ethane, a primary amine having the formula $R_1NH_2$, a secondary amine having the formula $R_2R_3NH$, $N(CH_2CH_2OH)_3$,

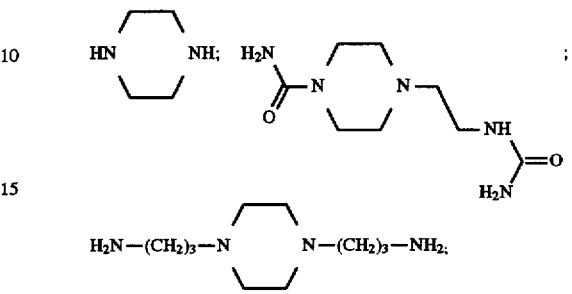

solubilized $NR_5R_6R_7$, $(CH_3)_2NCH_2CH_2N(CH_3)_2$, $R_8R_9NCH_2CH_2C(O)NH_2$, $R_{10}N(NCH_2CH_2C(O)NH_2)_2$, $R_{11}R_{12}N(CH_2)_3NHC(O)NH_2$, $N(CH_2CH_2NHC(O)NH_2)_3$, $[R_4—CH_2—CH_2—\overset{O}{\overset{\|}{C}}—NH\frac{1}{2}CH_2$, $+NH—(CH_2)_nNH—CH_2CH_2\overset{O}{\overset{\|}{C}}—NHCH_2NH\overset{O}{\overset{\|}{C}}CH_2CH_2\}_m$, or $+CH_2CH+\overset{O}{\overset{\|}{C}}—NH—CH_2CH_2CH_2N—(CH_3)_2\}_m$, wherein: $R_1$ is —$CH_2CH_2OCH_2CH_2OH$, —$C(CH_3)_2$ $CH_2OH$, —$CH_2CH_2NHCH_2CH_2OH$, —$CH(CH_3)_2$, —$CH_2CH_2OH$,

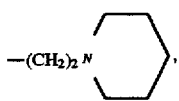

or

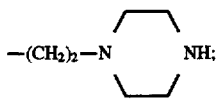

$R_2$ and $R_3$ are, independently, hexyl, benzyl, n-propyl, isopropyl, cyclohexyl, acrylamide, or —$CH_2CH_2OH$; $R_4$ is cyclohexyl or benzyl; $R_5$ and $R_6$ are methyl; $R_7$ is cyclohexyl or 4-pyridyl; $R_8$ and $R_9$ are, independently, methyl, n-propyl or isopropyl; $R_{10}$ is n-$C_6H_{13}$ or n-$C_{12}H_{25}$; $R_{11}$ and $R_{12}$ are, independently, methyl, ethyl, n-propyl or isopropyl; m is an integer from 1 to 100; and n is 2 or 3. Suitable diluents include formamide or acrylamide-isopropyl acrylamide. Oligomeric or polymeric secondary amines converted to acrylamide substituted tertiary amines by Michael reaction with acrylamides are also suitable because the amide group does not react with the acid releasing agent.

Hydroxylic compounds, including ethylene glycol, glycerin, methanol, ethanol, methoxyethanol, ethoxyethanol or other alcohols, can be used as the hydrophilic material. However, chlorine dioxide release can occur very rapidly when a hydroxylic compound is incorporated in the composite and can limit the applications for such composites to rapid chlorine dioxide releasing systems.

Suitable acid releasing agents include carboxylic acids, esters, anhydrides, acyl halides, phosphoric acid, phosphate esters, trimethylsilyl phosphate esters, dialkyl phosphates, sulfonic acid, a sulfonic acid esters, sulfonic acid chlorides, and phosphosilanes of glycerol based esters. Examples of such acid releasing agents include an anhydride or phosphate ester blended with or grafted to polypropylene, polyethylene or polystyrene, or trimethylsilyl phosphate esters of the formulae

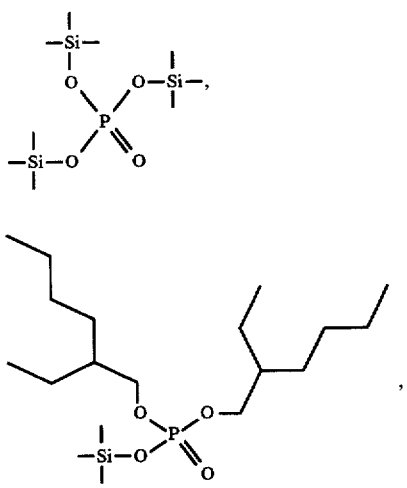

or $(CH_3)_3SiOP(O)(OR)_2$
wherein R is a non-hydrogen bonding group, alkyl or aryl.

Linear or star like oligomers (e.g., a micelle like molecule with a lipid wall and a P—O—Si core), such as a phosphosilane of a glycerol based ester, are preferred acid releasing agents because they can be melt- or solvent-processed with the option of being crosslinked after processing to provide film stability. A preferred phosphosilane of a glycerol based ester is known as LPOSI and has the formula

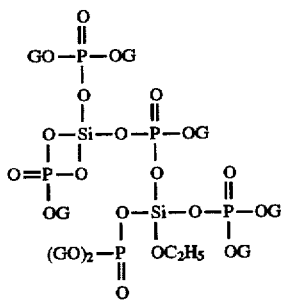

wherein G has the formula

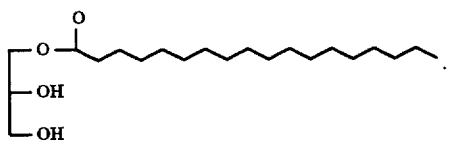

A free radical polymerizable alkene or condensible group on the terminal end of a lipid is a representative oligomer.

Acid anhydrides are also preferred acid releasing agents and include organic acid anhydrides, mixed organic acid anhydrides, homopolymers of an organic acid anhydride or a mixed inorganic acid anhydride, and copolymers of an organic acid anhydride or a mixed inorganic acid anhydride with a monomer containing a double bond. Preferred mixed inorganic acid anhydrides contain a phosphorus-oxygen-silicon bond. Preferred anhydrides include copolymers of maleic anhydride, methacrylic anhydride, acetic anhydride, propionic anhydride, or succinic anhydride, and vinyl, styrene or an alkene, such as maleic anhydride-styrene copolymers, or grafts thereof with olefins such as polypropylenes, polyethylenes, or polystyrenes. Copolymers of acid anhydrides and esters of lactic or glycolic acids can provide a rapid initial chlorine dioxide release rate followed by a slow release rate.

The hydrophobic material can further include a diluent such as atactic polypropylene, hydrocarbon wax, chlorinated wax, polyethylene wax, low molecular weight polyolefins, polyesters, derivatized polyolefin copolymers, or mixtures thereof. Diluents can be included in the hydrophilic material as well. Plasticizers can also be incorporated in either the hydrophobic or hydrophilic materials as is known in the art. Generally, formamide and isopropylacrylamide-acrylamide are acceptable plasticizers.

A moisture scavenger, such as sodium sulfate, calcium sulfate, silica gel, alumina, zeolites, and calcium chloride can be added to the composite to prevent premature hydrolysis of the acid releasing agent. Conventional film forming additives can be added to the hydrophobic and hydrophilic materials as needed. Such additives include crosslinking agents, flame retardants, emulsifiers and compatibilizers.

The composites of the present invention can be formulated in various ways to accommodate a wide range of end use applications. The composite can be formulated as an extrudate, such as a film or pellets, or as a powder using conventional extrusion and spray drying methods, respectively. When the composite is formulated as a powder, chlorite containing particles are formed by dissolving a chlorite source in a hydrophilic solvent and extruding the solution through nozzles of a spray dryer. Once the solution is transformed into spray dried particles, the particles can be routed to a cyclone separator to isolate small particles preferably having a diameter of between about 5 and about 150 microns. The particles can then be stored in a dry atmosphere. Once the chlorite particles are made, they are fed into a fluidized bed. The hydrophobic material containing the acid releasing agent is aerosolized by passing the material through small diameter nozzles into the chamber of the fluidized bed where it can impinge upon the fluidized chlorite containing particles. Upon contact with the fluidized particles, the chlorine dioxide releasing powder is formed as the hydrophobic material solidifies to form a hydrophobic core having a layer of chlorite particles embedded in the outer surface thereof. Aggregation is minimized because the chlorite particles are hard inorganic materials. The particles can then be packaged in a dry sealed container.

In forming the chlorine dioxide releasing powder, anhydrous particles, such as anhydrous sodium sulfate, calcium sulfate, magnesium sulfate, or a moisture depleted silica gel, can be included in the fluidized bed to form a mixture of chlorite particles and anhydrous particles. The anhydrous particles delay release of chlorine dioxide that is catalyzed by atmospheric moisture. The anhydrous particles can also be post-mixed with the chlorine dioxide releasing powder to delay chlorine dioxide release.

Although the hydrophilic and hydrophobic materials can be formulated as described above for the composite, it is preferred that the chlorite powder contains an alkali or alkaline-earth chlorite. The hydrophobic material preferably contains a low melting hydrocarbon wax, chlorohydrocarbon wax, atactic polypropylene, polyethylene wax, a low molecular weight polyolefin, derivatized polyolefin copolymer, or mixtures thereof. An acid releasing wax, such as a hydrocarbon solution of a phosphorylated lipoglycerol reacted with silicon alkoxides to produce mixed anhydride P—O—Si bonds, is preferred as the hydrophobic material. LPOSI is a particularly suitable acid releasing wax for use in preparing the chlorine dioxide releasing powder.

If the acid releasing wax is extruded at a viscosity between about 10 and about 1000 cP through nozzles of between about 1 and about 10 mil diameter, a fine spray of molten wax between about 5 and about 400 microns in diameter is generated.

In addition to formation of powdered composites, the composites of the present invention can be formulated in solvents to allow for film casting or other application methods. The composite can be applied as a film by using well known hot melt, dip coat, spray coat, curtain coat, dry wax, wet wax, and lamination processes.

Figure 3A:
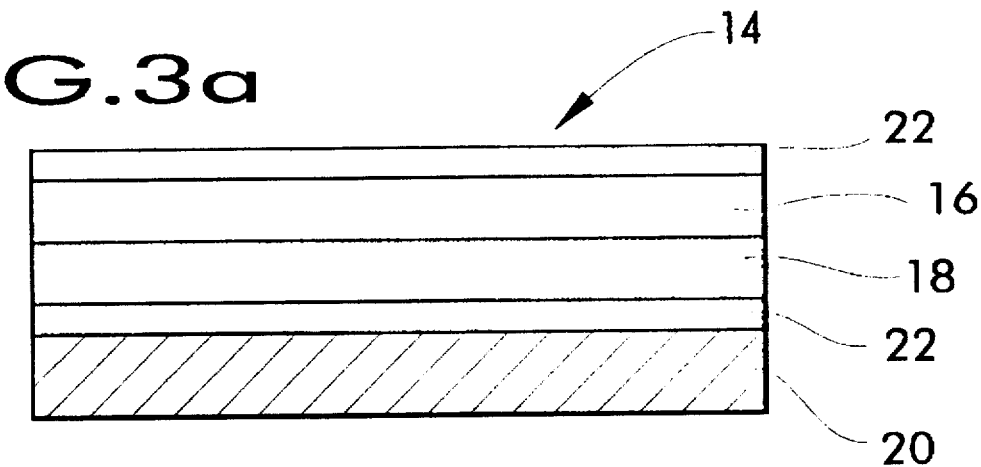
FIGS. 3a, 3b and 3c are schematics of multilayered composites for providing sustained release of chlorine dioxide.
Figure 3B:
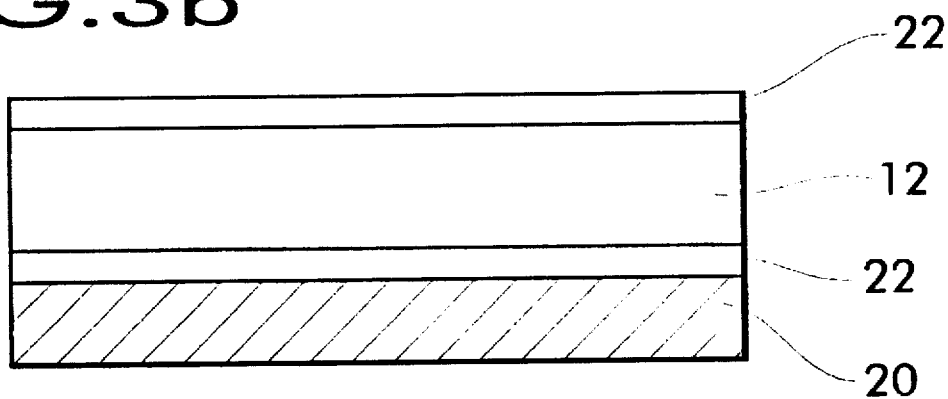

The composites can also be provided as a layer 12 composed of a microdispersed hydrophobic and hydrophilic material as shown in FIG. 3b, or as a multilayered composite 14 including a separate hydrophobic layer 16 and a separate hydrophilic layer 18 as shown in FIG. 3B. The hydrophobic and hydrophilic layers can be, applied by casting the hydrophilic layer onto a substrate 20 and then casting the hydrophobic layer onto the hydrophilic layer, as illustrated in FIG. 3B. The multilayered composite or single layer can be applied in conjunction with moisture regulating layers 22 to control the rate of moisture ingress into the hydrophilic material or hydrophobic material to control chlorine dioxide release from the multilayered composite when activated by moisture.

Figure 3C:
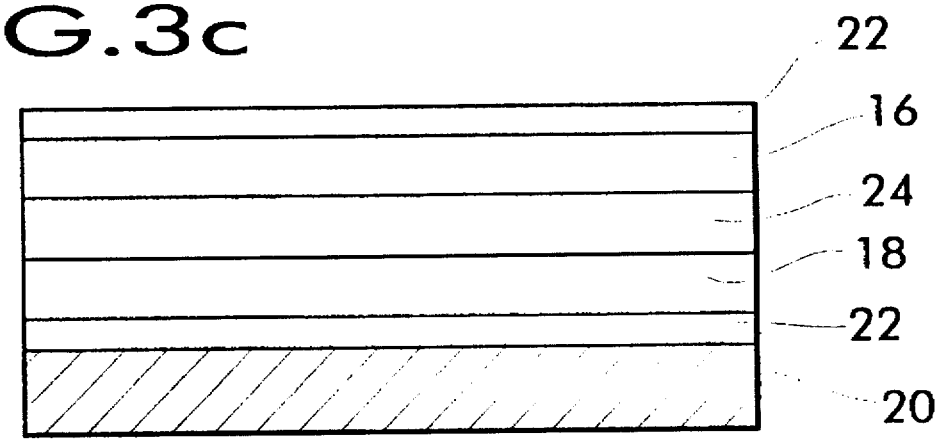

In order to generate chlorine dioxide in a controlled fashion it is useful to limit the access of water to the hydrophobic layer containing the acid releasing agent and to control the surface area of contact between the layer releasing the hydronium ion and the hydrophilic layer containing chlorite. Such controlled release can be obtained by casting the hydrophobic and hydrophilic materials 16, 18 as separate layers with an intermediate boundary layer 24 that regulates hydronium ion transport between the materials as shown in FIG. 3c.

The layered composites of the present invention are intended to maintain a desired rate of chlorine dioxide release (moles/secs/cm2 of film) in the presence of atmospheric moisture at a surface for a length of time required for chlorine dioxide to absorb onto the surface and kill bacteria or other microbiological contaminants. However, leakage from a container or exposed surface reduces the chlorine dioxide concentrations at the surface because of chlorine dioxide diffusion into the atmosphere. The chlorine dioxide concentration released from the film for a chosen time period can be calculated given the leakage rate and the rate of absorbance at a surface. Thus after measuring the leakage rate, the composite is formulated so that it contains a large enough reservoir of chlorite reacting at a speed sufficient to compensate for the leakage rate for the desired time period of sustained release.

Therefore, design of a chlorine dioxide releasing composite suitable for controlled release and biocidal action within a container must take into account several aspects, namely, the chlorine dioxide production rate from the controlled release film, the partitioning of chlorine dioxide between the phases within the container (e.g. gas, liquid and solid phases) in a reversible (absorbed) or irreversible (reacted) fashion, and the leakage rate of gas from the container. Design of such a composite is described in Example 15.

A preferred extended release system of the present invention conserves the chlorite reservoir by emitting a series of periodic pulsed releases timed to coincide with the suspected times of bacterial, viral or fungal contamination or the typical incubation time for the biological of interest. The system design can be optimized to maintain the desired kill concentration for the requisite time at the atmospheric chlorine dioxide leakage rates imposed by the specific application.

A typical controlled release multilayered composite includes water swellable films A and B of a thickness of about 5 mil with a hydrophobic layer A and a hydrophilic layer B as described above for the composite. The hydrophobic layer A contains an acid releasing agent such as an anhydride and hydronium ions generated by anhydride hydrolysis. The hydrophilic layer B contains chlorite anions as provided, for example, by dissolving sodium chlorite or another chlorite source in a hydrophilic solvent. The hydrophobic and hydrophilic layers are separated by a water swellable intermediate layer C having a thickness l (typically about 5 mil) and diffusion constant, D. The effective ion concentrations applied to the boundaries of intermediate layer C by the layers A and B are a strong function of the water transport properties of layer C.

The intermediate layer C can be composed of a wide variety of materials since chlorine dioxide can diffuse equally well in both hydrophobic and hydrogen bonded matrices. Such materials include polyionomers such as protonated and neutralized, sulfonated, or phosphorylated oligo- or poly-alkenes such as polyethylene, polypropylene, alkyl acrylates and copolymers thereof. Lipid substituted polyhydroxy alcohol phosphates and phosphosilicates and their mixtures with alkene polymers and oligomers are also preferred. Finely divided anhydrous salts or desiccants may be added to any of the layers to retard the reaction to chlorine dioxide that is catalyzed by water.

It has been discovered that construction of a multilayered composite wherein the arrangement of the layers in the composite is defined by the formula $C(ACB)_nC$ (wherein n represents the desired number of pulses) provides periodic pulsed release of high concentrations of chlorine dioxide over several weeks or months. Such pulsed release can be coordinated to the growth, incubation and contamination of viruses, molds, fungi and bacteria. The cycle time and peak concentrations of chlorine dioxide would be controlled by the layer thickness, chlorite and anhydride loading, and the water and ionic permeation characteristics of layers A, B and C. Pulsed release occurs as each layer $(ACB)_i$ is successively penetrated by water vapor and hydronium ions. Structures of type CDC can also be made where D is a mixture or emulsion of A and B of a phase size of between about 0.2 and about 100 microns. The materials of construction for the CDC composites can be the same as those used in making the $C(ACB)_nC$ composites. Additionally, a multilayered composite $C(DCD)_nC$ can be made in order to provide pulsed release as described above.

Pulsed releases of chlorine dioxide that vary from about one day to over about 200 days can be achieved for 5 mil thick A, B and C films by separating the hydrophobic layer A containing the acid releasing agent from the hydrophilic layer B containing chlorite anions by an intermediate layer C capable of supporting varying hydronium ion transport rates.

The pulsed release capabilities of a multiple layered film can be calculated as provided in Example 16.

Applications for the composites are numerous. The composites can be used in most any environment where exposure to moisture will occur. The composites can be used to prevent the growth of molds, fungi, viruses and bacteria on the surface of a material and/or deodorize the material by treating the surface with a composite that does not release chlorine dioxide in the absence of moisture, and exposing the treated surface to moisture to release chlorine dioxide from the composite into the atmosphere surrounding the material. The treated surface is generally a portion of a container or is part of a substrate placed within the container.

The biocidal atmosphere generated within the container can be used in storing food products including blueberries, raspberries, strawberries, and other produce, ground beef patties, chicken filets, and other meats, enhanced foods, pet foods, dry foods, cereals, grains, or most any food subject to bacterial contamination or mold growth. Bar soap, laundry detergent, stored paper documents, clothing, paint, and seeds can be protected from mold growth. Medical instruments, devices and supplies as well as disposable or nondisposable personal care products can be sterilized to prevent microbial contamination. Medical or biological waste can also be sterilized to kill microbials within the waste. Odors from athletic shoes, disposable footwear, and refuse can also be minimized when they are contained within a treated container.

Conventional containers can be used such as paperboard or containerboard boxes, corrugated, nonwoven, plastic, or polymeric multilaminate containers, cellulosic, plastic or paper bags, seed packets, or waste containers.

The treated surface can be a reusable or disposable mat or sheet including a dental tray covering, a surgical tray covering, a shower mat, nonwoven bandage material, a meat cutting board, a liner for drawers or shelves, an insert for athletic bags or gym lockers, a food wrapper, a paper sheet for separating hamburger patties, a meat packaging tray, an overpouch such as those used in packaging intravenous bags, a fresh fruit separator or box liner, an absorbent pad for poultry, meat, seafood or produce, or an absorbent layer for use in diapers. Such mats or sheets are typically made from paper, cellulosic, polymeric, woven fabric or nonwoven materials.

Such a method can also be used to coat the surface of a seed to protect the seed from molds and fungi during storage and to protect against mycotic growth when the seed is planted. The coating, when activated by moisture, creates a microatmosphere of chlorine dioxide in the soil in the vicinity of the seed and inhibits mycotic growth that normally would impede seed germination. This coating has no effect upon the germination of the seeds. Seeds in storage do not have to be physically coated to be protected but rather can be in a closed container containing the active material as a packet, "tea bag" or coating on the container. Paper impregnated with the composite generates sufficient chlorine dioxide to protect the seeds. Although any seeds can be protected by the coating, edible seeds such as corn kernels, sunflower seeds, or soybeans, remain fit for human consumption once they are coated. Thus, the coated seeds can be provided for planting or for human consumption after they have been coated.

The surface can be treated with any of the composites of the present invention by conventional coating, extrusion, lamination and impregnation methods well known in the art.

Another embodiment of the invention is a method of preventing the growth of fungi, bacteria or molds on a surface and/or deodorizing the surface by treating the surface with a composite that does not release chlorine dioxide in the absence of moisture, and exposing the treated surface to moisture to release chlorine dioxide from the composite into the atmosphere surrounding the surface.

A preferred application includes a foot powder for preventing athlete's foot and other fungi. The powder can be applied directly on the surface of the foot or can be incorporated into a shoe insert. The composite can be applied between the cloth covering and foam pad of the shoe insert, impregnated within the foamed pad, or impregnated or coated on a shoe counter or upper lining. Chlorine dioxide generated from moisture within the shoe diffuses from the composite into the atmosphere to kill fungus and deodorize the shoe. The powder can be blended with conventional ingredients such as talc, cornstarch, fragrance, miconazole nitrate, tolnastate silica, boric acid, aluminum chlorhydrate, salicylic acid, and cellulose. The powder can also be blended with other ingredients and used in bath powders or powders used in treating jock itch.

The powder can also be applied to carpeting to remove odors from the carpet. Ingredients commonly incorporated in powdered carpet deodorizers or cleaners can be blended with the powder of the present invention. The composite can also be formulated in microcapsules that break after being stepped on and are then activated by moisture. Such microcapsules can be impregnated in floor, shower or bath mats or can be used in carpet deodorization.

Another use for the composites is in providing self sterilizing packaging, which is particularly useful in the medical industry. The composite can be coated onto tubing, connectors, fitments or other components as separate layers of the hydrophobic or hydrophilic material on separate components that are activated upon being pressure fitted together. Tubing fitments used with intravenous bags, for example, can be treated such that a surface of one tube fitment is coated with a hydrophobic film containing acid releasing agent, a surface of another tube fitment is coated with a hydrophilic film containing chlorite, and the treated surfaces of the fitments are interconnected in the presence of moisture to initiate the release of chlorine dioxide from the treated surfaces into the atmosphere surrounding the material. Fitments for in-dwelling catheters, needles, peritoneal dialysis, percutaneous devices, percutaneous access, colostomy bags and other medical devices can also be treated in accordance with this method. Additionally, closures on a package can be so treated to provide self sterilizing packaging for medical devices, instruments and supplies.

The composite of the present invention was expected to kill bacteria on the surface of meats. However, it was not expected to penetrate a ground beef patty. It has been discovered that chlorine dioxide evolved from paper treated with the composite can effectively penetrate the full thickness of a patty and kill bacteria such as $E.\ coli$ and Salmonella that result from contamination during meat processing. $E.\ coli$ 0157:H7 in tainted meat has caused death and severe illness and appears to be especially resistant to cooking, fermenting and drying. In a typical operation producing meat patties for commercial consumption, meat is ground, extruded and formed into patties that are separated by sheets of coated paper that prevent adhesion of the individual patties. After packaging, the ground meat can be exposed to chlorine dioxide over a period of time when in refrigerated storage to kill and inhibit the growth of the bacteria.

The following examples are presented to describe preferred embodiments and utilities of the present invention and are not meant to limit the present invention unless otherwise stated in the claims appended hereto.

EXAMPLE 1

A hydrophilic material was made which contained a 7 wt. % solution of sodium chlorite in an amide mixture composed of 33 wt. % formamide, 33 wt. % acrylamide, and 33 wt. % isopropylacrylamide. A hydrophobic material consisting of a 40% solution of a copolymer composed of 33 mole % maleic anhydride and 66 mole % styrene in ethylbenzene plasticizer was then made. The hydrophobic material was vortex mixed with the hydrophilic material. The resultant white mixture of the two disperse materials started a sustained release of chlorine dioxide in the absence of added water within five minutes at room temperature. Interphase diffusion of water within the dispersion initiated hydrolysis of the anhydride. Hydronium ions formed during hydrolysis reacted with chlorite anions to release chlorine dioxide. The release rate could be slowed by cooling the mixture to 0° C. or by increasing the viscosity of the materials.

EXAMPLE 2

1-(N-dipropylamino)-2-carboxyamidoethane (DPACAE) was made by reacting 0.2 mole di(n-propyl)amine with 0.1 mole acrylamide in the presence of a small amount of acetic acid as a 10 wt. % solution in methanol. The reaction was carried out for 3 hours at 70° C. After vacuum evaporation of the excess amine and crystallization in the presence of pentane, a white low melting solid was obtained ($T_m$=60° C.) which tended to lose amine and form acrylamide upon prolonged heating above the melting point.

1-(N-Dimethylamino)-2-carboxyamidoethane (DMACAE) was made by reacting 0.2 mole dimethylamine (as a 40 wt. % solution in water) with 0.1 mole acrylamide as a 10 wt. % solution in methanol. The reaction was carried out for one hour at room temperature. After vacuum evaporation of excess amine, methanol and water, the DMACAE was taken up in methylene chloride, dried with magnesium sulfate and isolated as a low melting ($T_m$=45° C.) hydroscopic solid.

Both DPACAE and DMACAE crystallized only slowly and thus could be studied in the liquid state at room temperature. Neither neat liquid formed iminium chlorite. However, 10–30% wt. % solutions in formamide or acrylamide-isopropyl acrylamide readily formed iminium chlorite when exposed to chlorine dioxide.

EXAMPLE 3

The amine-chlorine dioxide reaction was studied by layering the requisite amount of $6.0 \times 10^{-5}$ molar solution of chlorine dioxide in pentane onto about $3.0 \times 10^{-4}$ mole of amine, either in neat form or dissolved 10–30 wt. % in formamide or isopropyl acrylamide-acrylamide melt. The chlorine dioxide-pentane solution was prepared by reacting stoichiometric sodium chlorite with potassium persulfate in a small amount of water in the presence of pentane with vortex stirring in ice water. The supernatant pentane layer was then removed and kept dry in a sealed container over magnesium sulfate.

The formation of chlorite was detected by acidification of the reaction product and the observation of the odor and color of chlorine dioxide by UV/Vis spectroscopy after exposure to dilute HCl. In some cases the presence of chlorite was further verified by observation of the IR spectrum. Characteristic IR absorbance of chlorite at 830 $cm^{-1}$ verified its presence.

The following neat primary amines formed chlorite when exposed to chlorine dioxide:
$H_2NCH_2CH_2OCH_2CH_2OH$, $H_2NC(CH_3)_2CH_2OH$, $H_2NCH_2CH_2NHCH_2CH_2OH$, $H_2NCH(CH_3)_2$, $H_2NCH_2CH_2OH$,

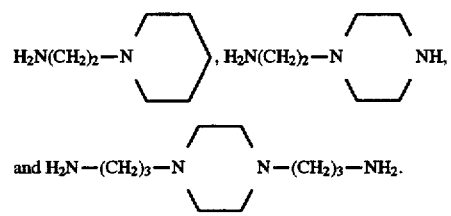

Chlorite was also formed by neat secondary amines having the formula $R_2R_3NH$ wherein $R_2$ and $R_3$ are, independently, hexyl, benzyl, n-propyl, isopropyl, cyclohexyl, acrylamide, or —$CH_2CH_2OH$. These amines also formed chlorite when the amine was in formamide solvent.

The following secondary amines yielded chlorite when plasticized with formamide or isopropylacrylamide-acrylamide:

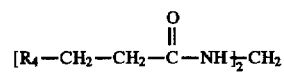

wherein $R_4$ is cyclohexyl or benzyl, and

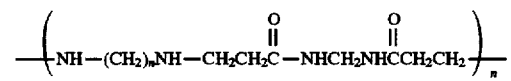

wherein n is 2 or 3. The isopropylacrylamide-acrylamide and amine were also prepolymerized and film formed by heating to 60°–70° C. in the presence of about 0.01% azobisisobutyronitrile initiator, providing chlorite so long as the film temperature exceeded the glass transition temperature.

A hydrogen bonded amine having the formula $R_8R_9NCH_2CH_2C(O)NH_2$ wherein $R_8$ is methyl and $R_9$ is n-propyl when in formamide or isopropylacrylamide-acrylamide solvent yielded chlorite. However, when $R_8$ and $R_9$ were isopropyl groups, the neat amine did not yield chlorite. A neat hydrogen bonded amine of the formula $N(CH_2CH_2OH)_3$ yielded chlorite, which was also formed when the amine was in formamide or isopropylacrylamide-acrylamide solvent.

To determine whether hydrogen bonding was necessary, a Michael addition process was used to provide a reaction product of 2-propenenitrile and (i-$C_3H_7$)$NHCH_2C_6H_5$ such that the amine portion of the product did not have any hydrogen bonding and the nitrile portion was very polar. Polarity was not sufficient to generate stable chlorite when the neat amine or the amine solvated in formamide was exposed to chlorine dioxide. The nitrile group blocked formamide so that the chlorite back attacked the amine and decomposed the chlorite into a form that could not be reconverted to chlorine dioxide. Thus, it was discovered that amines in apolar environments react with chlorine dioxide but the chlorite ion is unstable in such an environment.

Non-hydrogen bonded tertiary amines of the formula $NR_5R_6R_7$ wherein $R_5$ and $R_6$ are methyl and $R_7$ is cyclohexyl or 4-pyridyl were solubilized in formamide or isopropylacrylamide-acrylamide and formed a stable chlorite. Amines wherein $R_5$ is benzyl, $R_6$ is cyclohexyl and $R_7$ is dodecyl or wherein $R_5$, $R_6$ and $R_7$ are n-butyl or ethyl groups were insoluble in formamide and could not form any chlorite. $(CH_3)_2NCH_2CH_2N(CH_3)_2$ was soluble in formamide and yielded chlorite, but did not yield chlorite in isopropylacrylamide-acrylamide although it was solubilized by the solvent; the amine when neat or in acetonitrile did not yield chlorite.

Thus, it was discovered that an amine having a nitrogen of sufficiently high $pK_a$ solvated by a hydrophilic material or substituted by hydrogen bonding groups, such as hydroxylic, amide, primary amine or secondary amine substituents, forms chlorite by reaction with chlorine dioxide.

The amine-chlorine dioxide reaction as described above was repeated wherein the amine was dissolved in various solvents to determine the effect of the solvent on reaction efficiency. All chlorine dioxide was released in water. More chlorine dioxide was released in glycerin or ethylene glycol than was released in methanol, acetonitrile, methoxyethanol, ethanol or ethoxyethanol. Chlorite suspended or dissolved in a hydrophobic material, as a dilute solution in toluene or benzene, and exposed to chlorine dioxide reacted with chlorine dioxide but only released a minor amount of chlorine dioxide when acidified. Many of these solvents, such as ethanol, will not retain chlorite counterion for long term storage unless iminium chlorite is stabilized with a strong base to retain the chlorite counterion.

EXAMPLE 4

Amines that are monosubstituted with short apolar groups, such as $(CH_3)_2NCH_2CH_2C(O)NH_2$, $(n-C_3H_7)_2NCH_2CH_2C(O)NH_2$, and $(i-C_3H_7)_2NCH_2CH_2C(O)NH_2$, formed stable chlorite in formamide. Amines that were substituted with short apolar groups, namely $(CH_3)_2NCH_2CH_2C(O)NH(i-C_3H_7)$, $(n-C_3H_7)NCH_2CH_2C(O)NH(i-C_3H_7)$ and $i-C_3H_7N(CH_2CH_2C(O)NH_2)_2$, did not form stable chlorites. However, those with linear alkane lengths greater than or equal to six, such as $n-C_6H_{13}N(CH_2CH_2C(O)NH_2)_2$ and $n-C_{12}H_{25}N(CH_2CH_2C(O)NH_2)_2$, did form stable chlorite in formamide. It is possible that once the apolar chain length had achieved a certain length, a microphase separation into micelles with discreet hydrophobic regions surrounded by continuous hydrophilic regions took place. The destabilizing apolar phase was thus removed from the reaction environment.

EXAMPLE 5

The following polymers were synthesized, characterized using NMR techniques, and evaluated to determine physical properties and ability to uptake (and release) chlorine dioxide:

[—$CH_2CH_2N(CH_2CH_2CH_3)$—]$_n$

[—$OCH_2CH(CH_2N(CH_3)_2)$—]$_n$

[—$CH_2CH(OCH_2CH_2N(CH_3)_2)$—]$_n$

[—$CH_2CH(C(O)N(H)CH_2CH_2CH_2N(CH_3)_2)$—]$_n$

Of these polymers, the last polymer has the most flexible amine containing side group and exhibited the most efficient uptake and release of chlorine dioxide in formamide that is a substantial improvement over that demonstrated with in-chain amines. The polymer was also soluble in molten urea.

EXAMPLE 6

The following compounds containing an N-amido linkage and a tertiary amine center were synthesized in pure form from the corresponding primary or secondary amine, sodium cyanate, and hydrochloric acid as described by J. March, "Advances in Organic Chemistry: Reaction Mechanisms and Structure, 4th Ed., John Wiley, N.Y., p. 903 (1992).

$Me_2N(CH_2)_3NHC(O)NH_2$
HNMR: 1.5, 2.1, 2.2, 2.95, 5.5, 6.2
$N(CH_2CH_2NHC(O)NH_2)_3$
HNMR: 2.4, 3.0, 5.65, 6.25

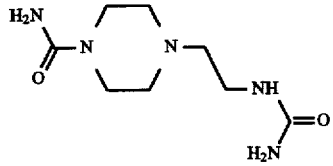

HNMR: 2.35, 3.2, 5.6, 6.05 ppm

Each of these compounds reacted with chlorine dioxide and later released it upon acidification in formamide, indicating that tertiary amine compounds with N-amido substitution of their primary and secondary amines can complex chlorine dioxide, when dissolved in a suitable hydrophilic solvent. Addition of urea to the formamide clearly improved the uptake and release efficiency.

EXAMPLE 7

Up to 50 wt. % of the tertiary amine dimethylaminoacrylamide (DMAA) was added to hydrophilic solvent containing 50 wt. % urea and 50 wt. % n-methylacetamide (NMA) solvent at 50° C. and quickly cooled to room temperature. The solution remained single phase indefinitely at room temperature. The same behavior was noted for the addition of 20 wt. % DMAA to a solvent containing 33 wt. % urea, 33 wt. % NMA and 33 wt. % sodium acetate, a solvent containing 35 wt. % urea, 55 wt. % NMA and 10 wt. % sodium methoxide, and a solvent containing 70 wt. % urea and 30 wt. % sodium acetate.

The above mixtures were exposed to a solution of chlorine dioxide in pentane and were observed to rapidly uptake (one minute) one chlorine dioxide for every two amine groups before the reaction slowed substantially. The final pH of the hydrophilic material remained on the basic side. A slight cloudiness was seen in the 50 wt. % urea/50 wt. % NMA-DMAA mixture and the 33 wt. % urea/33 wt. % NMA/33 wt. % sodium acetate—DMAA mixture while the DMAA—35 wt. % urea/55 wt. % NMA/10 wt. % sodium methoxide mixtures remained clear.

Upon acidification by 0.1N HCl (pH<5), complete release of chlorine dioxide from all three mixtures was observed up to 30 minutes after formation of the chlorite salt. The release of chlorine dioxide was estimated by referring to the color of solutions containing known amounts of chlorine dioxide. After this time different behavior was observed. For example, after two hours, the 50 wt. % urea/50 wt. % NMA-DMAA mixture released no chlorine dioxide. The 33 wt. % urea/33 wt. % NMA/33 wt. % sodium acetate completely released chlorine dioxide after two hours at room temperature. However, only one third of the chlorine dioxide was released after 24 hours at 5° C., with no chlorine dioxide being yielded after an additional 24 hours at room temperature.

35 wt. % urea/55 wt. % NMA/10 wt. % sodium methoxide exhibited the greatest chlorite salt stability in that complete release was noted after three days storage at 5° C. Complete release was also noticed after 24 hours at room temperature. The presence of a strong inorganic base greatly improves the stability of the chlorite salt in urea based solvents.

A 20% DMAA—35 wt. % urea/55 wt. % NMA/10 wt. % sodium methoxide melt was examined at 60° C. for up to one hour in 300 MHz proton NMR to see if any DMAA decomposition occurred. From the toxicological point of view any decomposition of the DMAA into secondary amine and toxic acrylamide would be highly undesirable.

No decomposition was observed over the one hour heating period. Acrylamide alkene resonances were expected between 6–4 ppm yet none were seen. Some polymerization of the urea was revealed by the broad band under a sharp urea band at 6–7 ppm. The NMR obtained after heating at 120° C. for two hours, much above the 50° C. at which the DMAA was mixed into the urea based solvent, revealed extensive polymerization of the urea that was evident from the increase in line width and the complication in the urea resonance between 8 and 6 ppm. However, no alkene acrylamide resonances were seen. Thus, the 20% DMAA— 35 wt. % urea/55 wt. % NMA/10 wt. % sodium methoxide system produced no toxic alkene products.

To avoid variability in chlorite stability from incomplete drying of the solvent, 40 wt. % of carefully dried urea (vacuum dried: 80° C., 18 hours, 0.1 torr) and 60 wt. % NMA (CaO overnight reflux and distilled) were mixed and heated for 18 hours at 120° C. Alkoxides were first isolated as dry powders by reacting the required amount of clean sodium metal with the alcohol and isolating the product by washing with diethyl ether. All mixing was carried out under dry nitrogen atmosphere. Predrying of the urea/NMA mixture resulted in room temperature stability of the iminium chlorite salts for at least one week at room temperature.

The desired amount of alkoxide was then dissolved in the urea/NMA solvent using minimal heating followed by DMAA to form a clear viscous liquid at room temperature. The results of the chlorine dioxide uptake and release of several urea/NMA/DMAA/sodium alkoxide hydrophilic material composites are presented in Table 1. Release characteristics are based on a relative scale ranging from excellent (9) to poor (1).

The presence of an alkoxide promotes long term iminium chlorite stability. However, the addition of more than 0.5 mole chlorine dioxide per mole of amine substantially decreased iminium chlorite stability.

Excellent long term stability was found at room temperature for the phases containing 23% sodium ethoxide, 31% sodium isopropoxide or 30% sodium t-butoxide, in that at least 60% of the chlorine dioxide was released upon acidification of the phase after three weeks storage in dry, dark conditions. Since no change in the chlorine dioxide release was noted after one week, these phases were considered indefinitely stable after one week.

EXAMPLE 8

In order to make a hydrophobic acid releasing wax, hydrocarbon wax ($T_m$=60° C.) or atactic polypropylene (APP) was first melted at 70° C. under nitrogen with stirring. An equivalent weight of glycerol monostearate or glycerol distearate was then dissolved in the molten wax or APP. Two equivalents (based upon phosphorous) of powdered phosphorous pentoxide per three equivalents of glycerol compound hydroxyl functions was slowly added to the melt to avoid clumping. After stirring the melt an additional two hours at 80° C., one equivalent of tetraethylorthosilicate was added and the immediate evolution of ethanol was detected. Stirring was continued for an additional four hours while slowly raising the temperature to 100° C. and purging the mixture of ethanol with a 10 cc/minutes flow of nitrogen. The reaction flask was subsequently evacuated at 100° C. to remove any remaining ethanol or tetraethoxysilicate, filled with nitrogen and cooled. Softening of the wax-acid releasing agent (LPOSI) started at about 60°–70° C. The viscosity of the wax was 100 cP at 100° C.

The process for preparing LOPSI can be summarized as follows. When hydrolyzed, silicon dioxide and a phospholipid are formed.

TABLE 1

| Sodium Alkoxide[a] | % Alkoxide | % Amine[b] | Equiv. $ClO_2$[c] | Day 0 | Day 1 | Day 2 | Day 3 | Day 4 | Day 5 | Day 6 | Day 7 |
|---|---|---|---|---|---|---|---|---|---|---|---|
| — | 0 | 30–50 | 0.5 | 9 | 0 | 0 | 0 | 0 | 0 | 0 | 0 |
| C1 | 7 | 20 | 0.5 | 9 | 4 | 0 | 0 | 0 | 0 | 0 | 0 |
| C1[d] | 15 | 20 | 0.5 | 9 | 4 | 0 | 0 | 0 | 0 | 0 | 0 |
| C2 | 23 | 20 | 0.5 | 9 | 8 | 7 | 7 | 7 | 6 | 6 | 5 |
| C2 | 30 | 22 | 0.75 | 3 | 2 | 1 | 1 | 1 | 1 | 1 | 1 |
| i-C3 | 20 | 20 | 0.5 | 9 | 8 | 7 | 6 | 5 | 5 | 3 | 3 |
| i-C3 | 31 | 27 | 0.5 | 9 | 9 | 8 | 8 | 7 | 7 | 6 | 5 |
| t-C4 | 16 | 30 | 0.5 | 9 | 8 | 7 | 4 | 4 | 2 | 2 | 1 |
| t-C4 | 30 | 23 | 0.5 | 9 | 9 | 8 | 8 | 7 | 7 | 6 | 6 |
| $NaClO_2$ | 7 | — | — | 9 | 9 | 9 | 9 | 9 | 9 | 9 | 9 |

[a]Methyl and t-butyl alkoxides are commercial products.
[b]Percentages are based on material already present in the mixture at that stage and not the final composite.
[c]Based on amine
[d]These experiments were done without predrying of the urea and NMA.

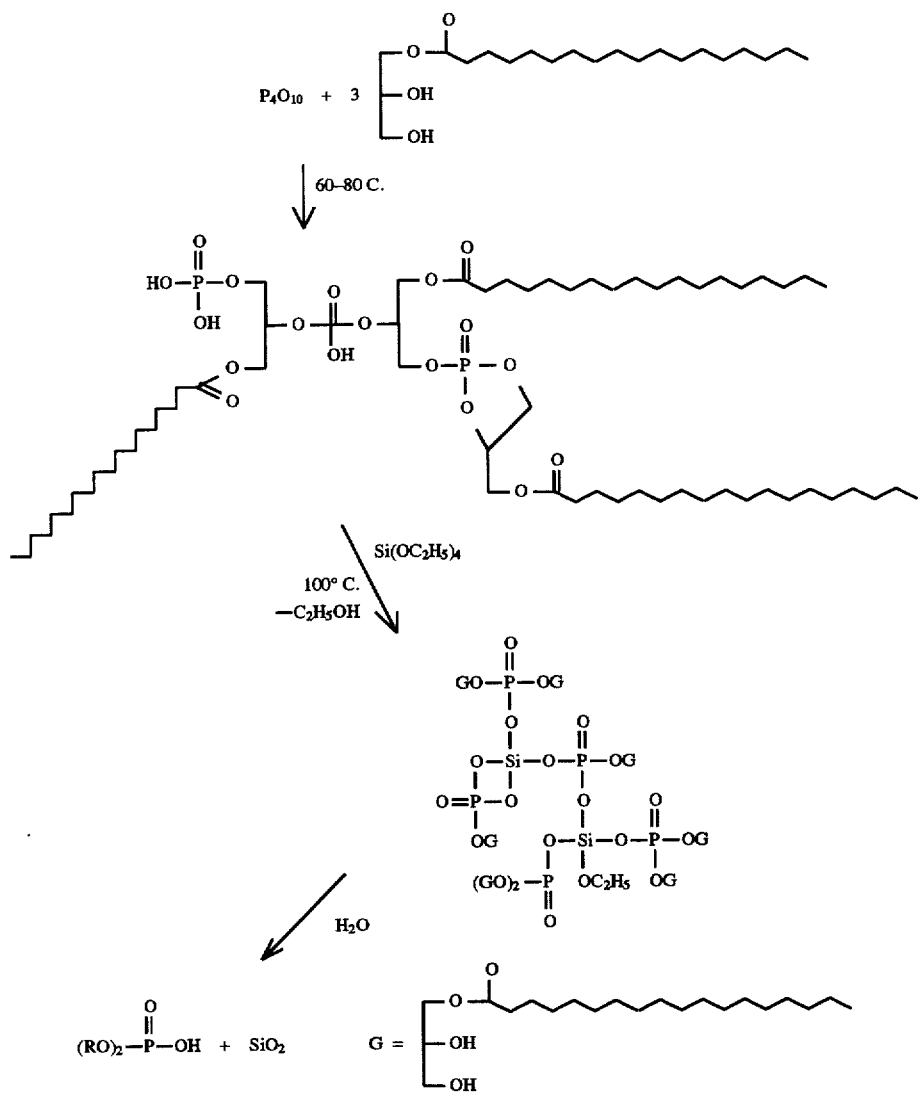

Chlorite powder was prepared by first dissolving commercial sodium chlorite in dry methanol at 3% by weight and filtering the resultant solution to remove sodium carbonate impurity. The chlorite solution was then extruded into an anhydro spray drier in dry nitrogen at 100° C. through a self siphoning extrusion head with co-axial fluid and nitrogen flow. After routing to a cyclone separator to isolate small sodium chlorite particles of about 5 microns in diameter, the powder was stored in a dry atmosphere.

Neat sodium chlorite powder or mixtures of sodium chlorite powder and anhydrous sodium sulfate in a ratio of 1:1 and 1:2 by weight was fluidized in the bottom of a nitrogen filled container. A stream of acid releasing wax was then directed into the fluidized bed through a nozzle of 7 mil in diameter with a nitrogen back pressure of 30–80 lbs/in$^2$ to produce wax particles encapsulated with chlorite and sulfate particles (indicated as 1:1 pre and 2:1 pre in FIG. 4). The freely flowing powders were then stored in a dry atmosphere. In some cases anhydrous sodium sulfate was post-mixed with the chlorite-wax particles (i.e., 1:1 post and 2:1 post in FIG. 4).

Figure 4:
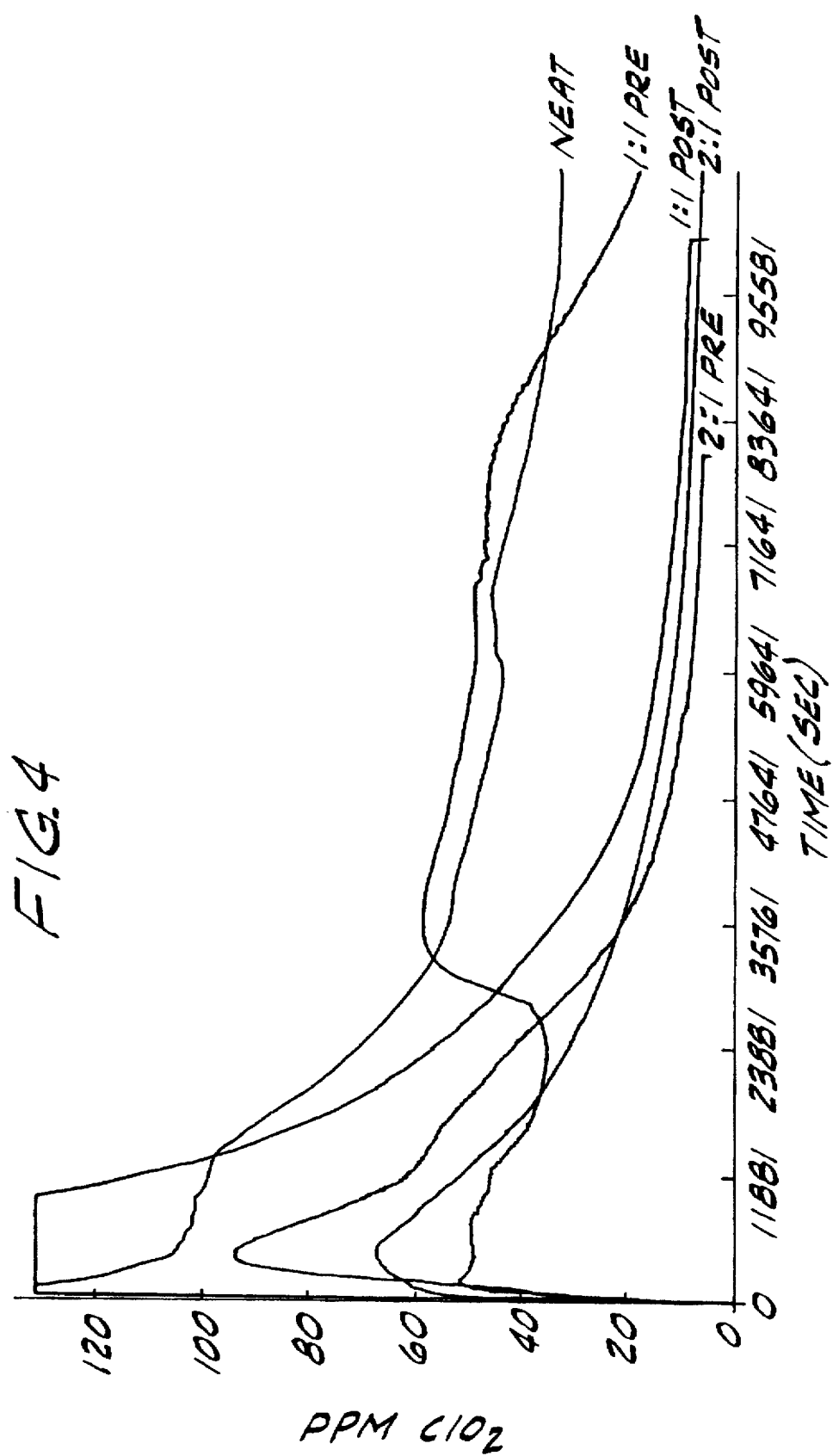
FIG. 4 is a plot of chlorine dioxide release rates for several powder compositions.

FIG. 4 shows the chlorine dioxide release rate from 200 mg of several powder composites placed in a Petri dish of approximately 62 cc volume with a leakage of 2×10$^{-9}$ moles/sec. Controlled release over several days is accomplished at about 75° F. and 40% relative humidity.

EXAMPLE 9

A hydrophobic acid releasing wax was made as described in Example 8. The controlled release layer for an immediate release system was formulated by melt coating approximately 5 mil of acid releasing wax in a low melting hydrocarbon wax (60° C.=$T_m$) onto both sides of a piece of paperboard. Next, approximately a 5 mil thick layer of 10% by weight, methanol recrystallized, sodium chlorite in the low melting wax was melt coated onto the acid releasing layer. Another acid releasing layer of about 5 mil thickness was then coated onto the chlorite containing layer. The total volume of controlled release material was 0.25 cc.

Two chlorine dioxide measuring sensors (0–10 ppm and 0–100 ppm) were interfaced with a computer so that chlorine dioxide concentration was recorded as a function of time over a two week period automatically along with humidity and temperature. Both sensor ends were exposed to the chlorine dioxide atmosphere in a closed Petri dish through two small holes drilled into the top cover of the Petri dish. The humidity and temperature in the room were close to that measured in the Petri dish because the Petri dishes were of the "breathable" type where the cover made contact with the base at a serrated edge and no effort was made to insulate the Petri dish from its surroundings.

Figure 5:
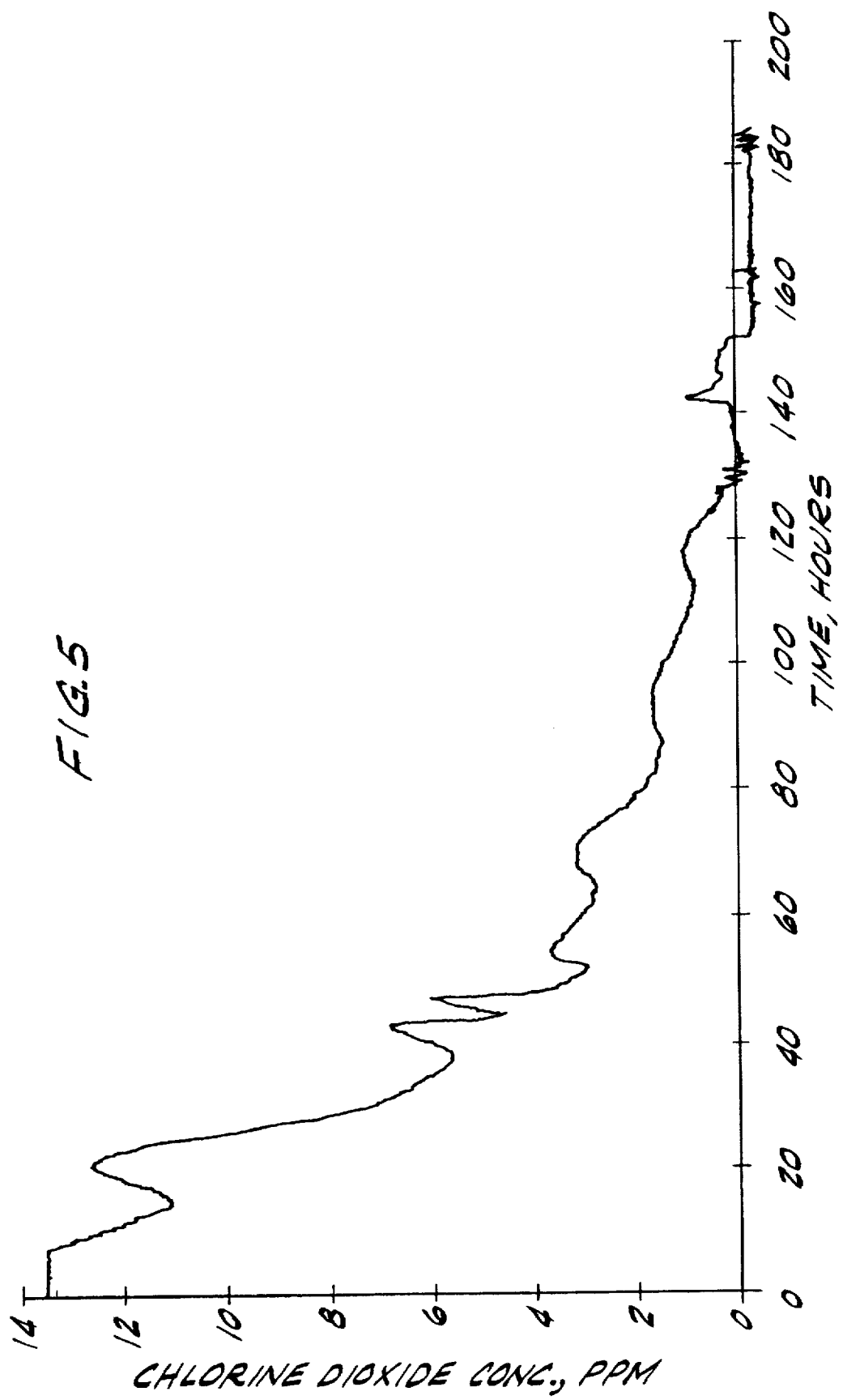
FIG. 5 is a plot of chlorine dioxide release rates for a layered composite.
Figure 6:
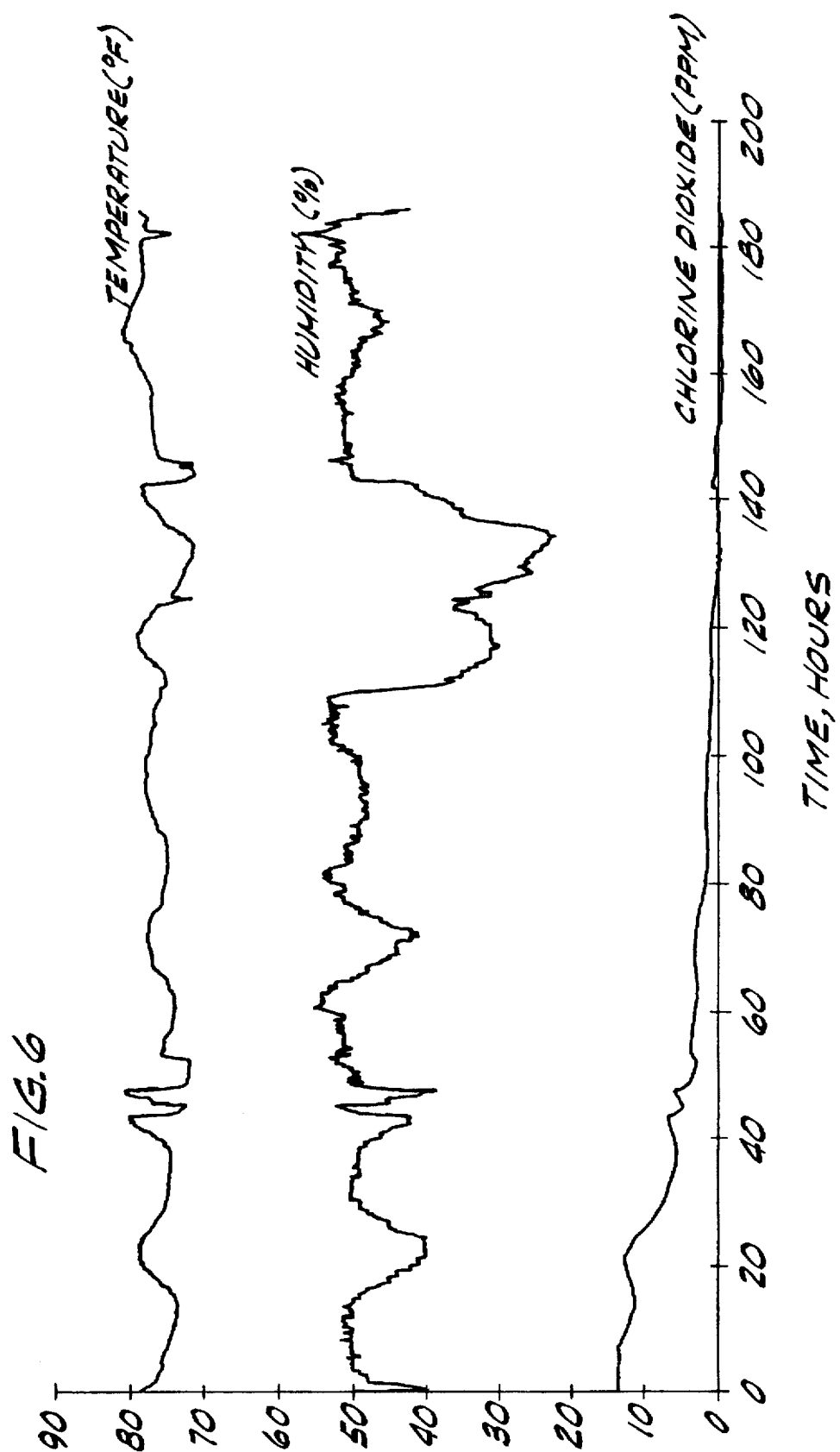
FIG. 6 is a plot of chlorine dioxide release rates in relation to atmospheric temperature and humidity.

In this configuration, the acid releasing layer was placed in direct contact with the chlorite containing phase and immediate release of chlorine dioxide was observed as soon as the film was placed in the Petri dish. The chlorine dioxide gas concentration dropped from a high of 13 ppm to 1 ppm at 5–6 days in an exponential fashion as shown in FIG. 5 (note that detector error of ±0.5–1.0 ppm resulted in less than zero concentration). However, surprisingly, the concentration peaks that were superimposed upon this exponential behavior, were correlated with the temperature and not the relative humidity as shown in FIG. 6.

Three mold species, *Chaetomium globosum* (CG), *Aspergillus terreus* (AT), and *Aspergillus niger* (AN), were grown in mineral loaded, but nutrient free agar slants using paperboard as a nutrient. All growth studies were carried out in accord with TAPPI standard method T 487 pm-85 entitled "Fungus Resistance of Paper and Paperboard."

Six samples were tested for fungus resistance over two weeks at room temperature in duplicate. Photographic comparisons showed considerable growth after two weeks on the control samples, while no growth showed on the controlled release films. The effectiveness of chlorine dioxide in killing these three molds was evident from the two week study.

EXAMPLE 10

In a delayed release system one side of a piece of paperboard was coated with an acid releasing layer separated from a chlorite layer by an intermediate wax layer. The 5 mil thick hydrophilic phase in the chlorite layer was a transparent blend containing 10 wt. % sodium chlorite, 50 wt. % $(NH_2C(O)CH_2CH_2OCH_2CH_2)_2O$ and 40 wt. % formamide. The chlorite layer was separated from the acid releasing LPOSI wax of about 5 mil thickness by an unmodified wax layer of about 5 mil thickness. The total volume of controlled release material was about 0.25 cc.

Figure 7:
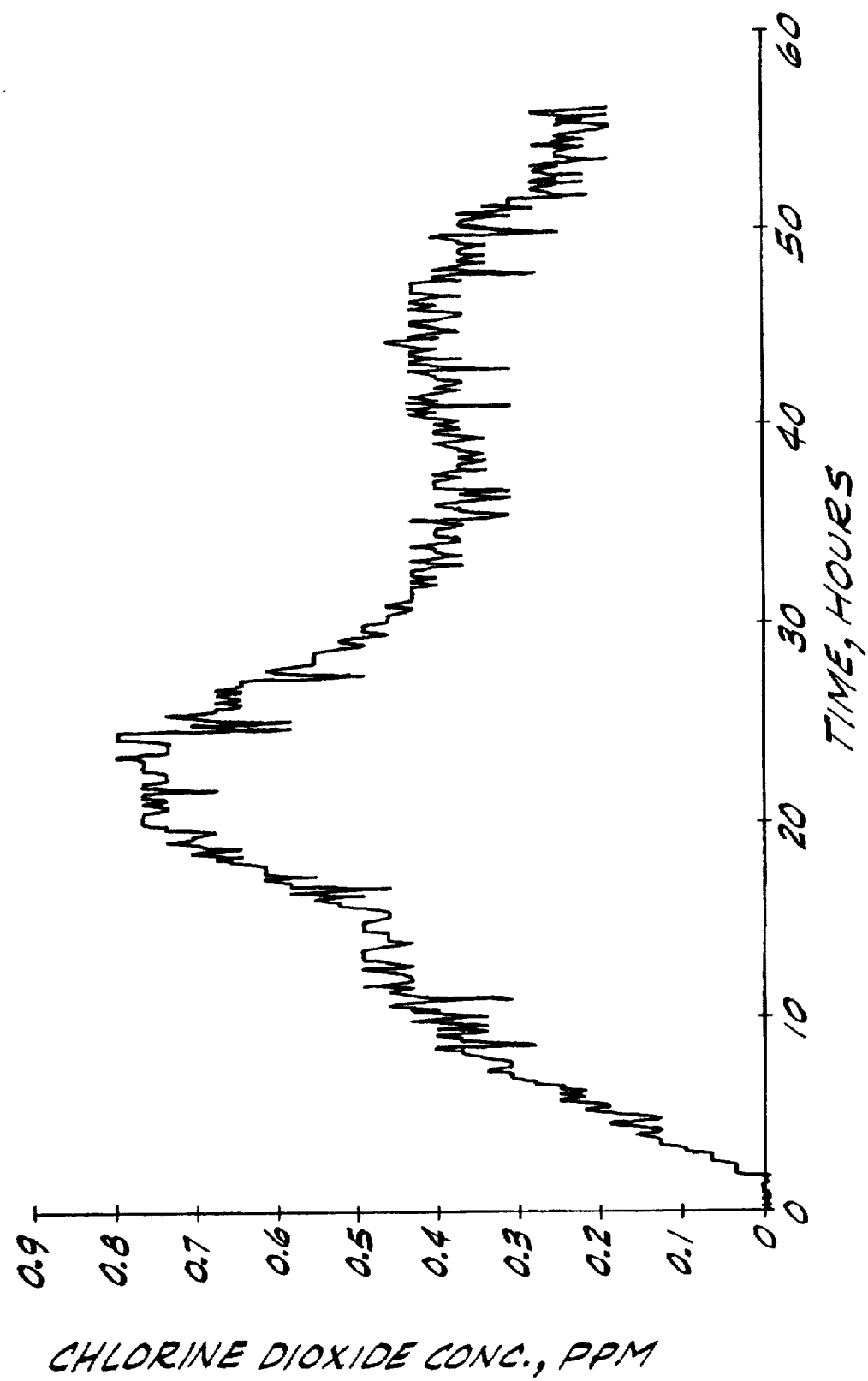
FIG. 7 is a plot of chlorine dioxide release rates for a layered composite.
Figure 8:
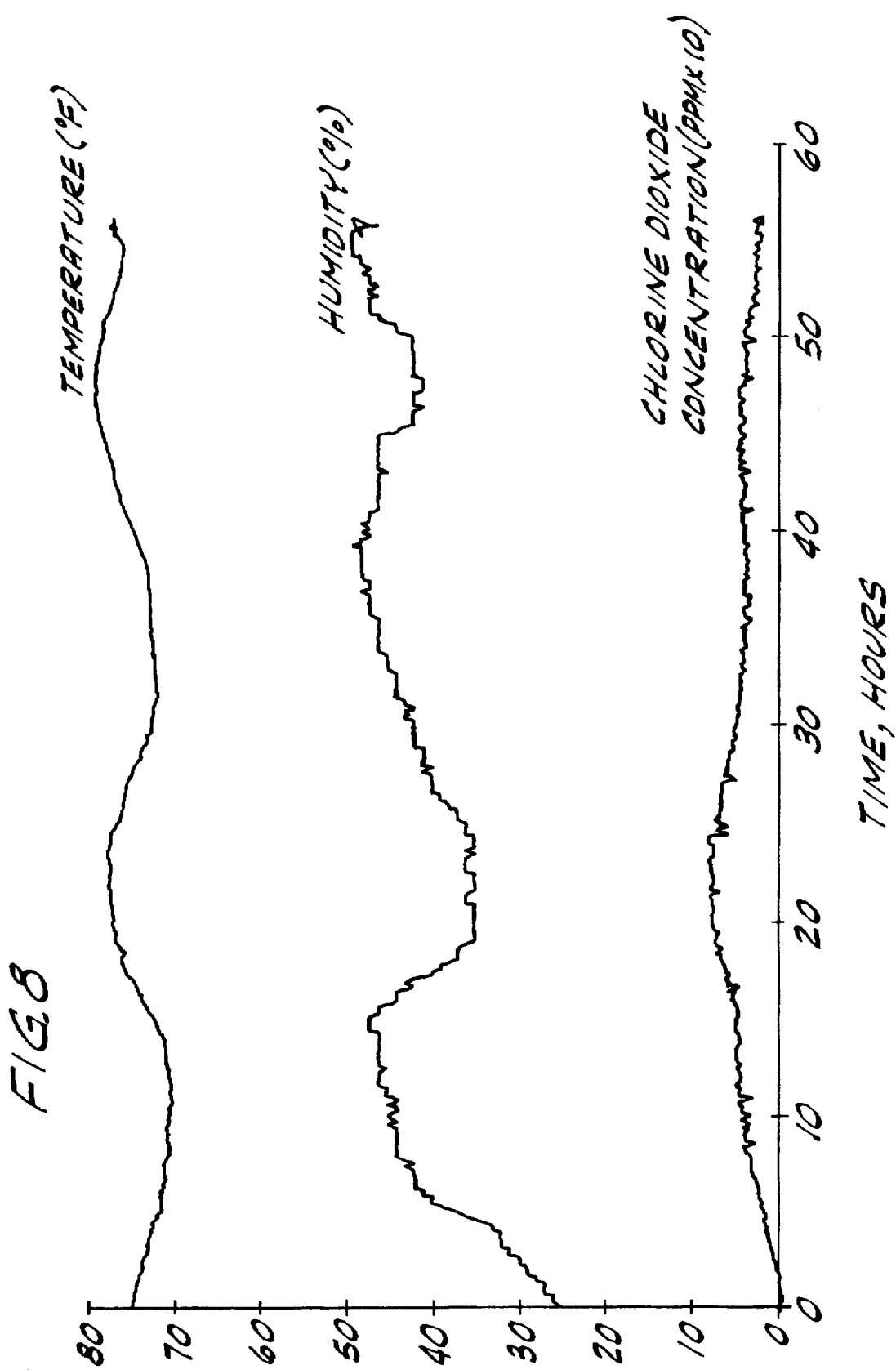
FIGS. 8 and 9 are plots of chlorine dioxide release rates in relation to atmospheric temperature and humidity.

A delay in chlorine dioxide release was noted when the acid releasing layer was separated from the chlorite containing layer by an intervening wax layer. In this case, a peak in the release was noted after one day as shown in FIG. 7. Individual concentration peaks superimposed on the averaged behavior were again correlated with the temperature and not with the humidity as shown in FIG. 8.

The three mold species tested for in Example 9 were grown in mineral loaded, but nutrient free agar slants using paperboard as a nutrient in accord with TAPPI standard method T 487 pm-85.

Six samples were tested for fungus resistance over two weeks at room temperature in duplicate. The results are presented in Table 2. Photographic comparisons showed considerable growth after two weeks on the control samples, while most of the controlled release films showed no growth. In the few cases where mold did grow on the controlled release films, only a single nucleus was responsible. Invariably, this nucleus was a large clump of mold spores where some self protective effect was generated by the aggregate structure.

TABLE 2

|  | CG Mold | AT Mold | AN Mold |
| --- | --- | --- | --- |
| Control Lawns[1] | Growth Growth from single mold spore | Growth No growth | Growth No growth |
| Soak[2] | Growth from single mold spore | No growth | Growth from single mold spore (trial 1), No growth (trial 2) |

[1]Agar covered with mold spores
[2]Paper soaked in mold spores

EXAMPLE 11

The porous paper used throughout these examples had one untreated side and one side that appeared glossy. The chlorine dioxide release coatings were applied to the untreated side of the paper with the chlorine dioxide releasing composite sheets assembled with the glossy side out. Consequently, only the glossy side of the paper had contact with the meat. Sheets approximately 3 ft.×8 in. were cut to facilitate handling during the coating process. The original paper weight was 5 mg/cm².

LPOSI acid releasing wax was applied to the porous substrate paper in a nitrogen filled dry box containing a large dish of stirred phosphorus pentoxide using a wax coater operating at approximately 190° F. If multiple coatings were used, the paper was allowed to cool prior to applying subsequent layers. Once the paper was coated, it was sealed in a dry atmosphere suitable for storage.

The chlorite containing paper was applied from methanol solution using a coater operating at room temperature. A typical coating solution was prepared by first dissolving 25 grams of poly N-vinyl pyrrolidinone (PVNP, $1.7 \times 10^6$ M.W.) in 500 ml of methanol followed by 15 grams of sodium chlorite (technical grade). The homogeneous solution was used immediately. If multiple coatings were desired on a single substrate, the coating was allowed to dry between applications. The chlorite containing paper was then sealed in dry atmosphere for storage.

Immediately prior to use, the chlorite containing film was compression molded at room temperature with the LPOSI containing film to form a chlorine dioxide releasing bilayer composite. Pressures under 10,000 lbs/in² were sufficient to induce cold flow and adhesion of the wax to the chlorite containing film.

Samples of each individual sheet of coated substrate bilayer were randomly set aside during the pressing operation in order to quantify the chlorite and wax loadings. These sheets were cut, measured and weighed, then compared with data obtained from uncoated paper as shown in Table 3. Calculations of the theoretical acid output based on phosphorous pentoxide and the relation:

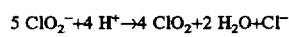

$$5 ClO_2^- + 4 H^+ \rightarrow 4 ClO_2 + 2 H_2O + Cl^-$$

indicate a ratio of approximately 0.14 g $NaClO_2$/g wax for optimum $ClO_2$ utilization.

TABLE 3

| Sample (ClO$_2$:Wax) | # ClO$_2$/ PVP coatings | NaClO$_2$ (mg/cm$^2$) | # Wax coatings | Wax (mg/cm$^2$) | $\dfrac{\text{g NaClO}_2}{\text{g Wax}}$ |
| --- | --- | --- | --- | --- | --- |
| 1:1 | 1 | 0.44 | 1 | 2.9 | 0.15 |
| 3:6 | 6 | 1.6 | 3 | 6.3 | 0.25 |
| 2:4 | 4 | 1 | 2 | 5 | 0.21 |
| 2:2 | 2 | 0.45 | 2 | 4.7 | 0.096 |

Figure 9:
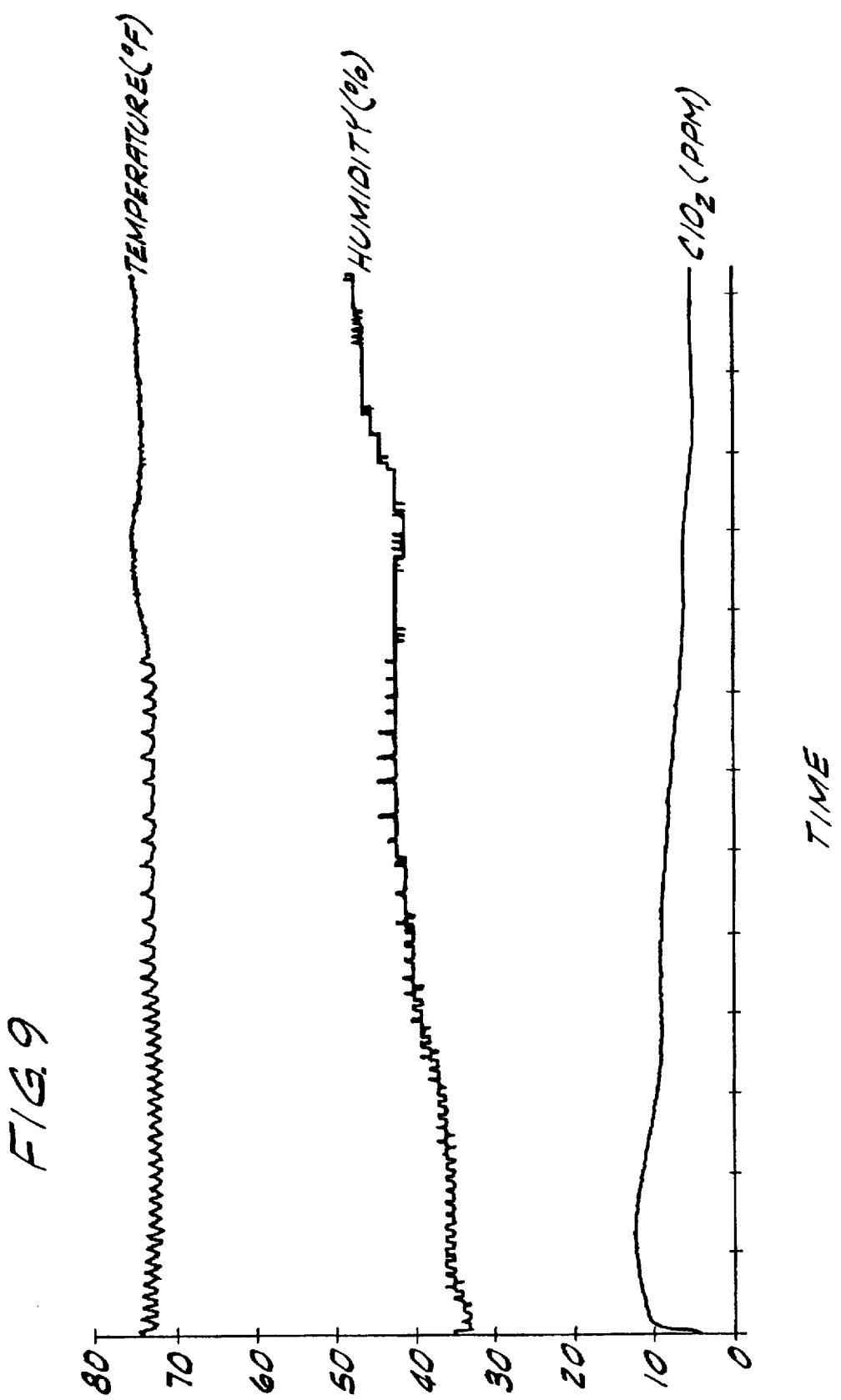

The chlorine dioxide concentration released from the films along with humidity and temperature was monitored in a Petri dish under atmospheric conditions using the sensor system and gas leakage rate previously described in Example 9. Samples were monitored over several days. FIG. 9 shows a typical plot generated from data acquired from a sample composed of sheets with two coats of each phase (2:2). Samples were monitored at several different loading levels. All samples showed an immediate maximum release of 10–20 ppm chlorine dioxide within the first 2–3 hours followed by a very gradual reduction in release over the next several days. Higher loadings served to increase the maximum initial concentration and prolong the release.

EXAMPLE 12

2:2 loaded papers were used as separators between ground meat patties packed to different densities that were loaded initially with high loadings of colony forming units (CFU) of *E. coli* bacteria. Substantial reductions in bacterial growth were noted as shown in Table 4. In loosely packed patties, the chlorine dioxide gas had access to the interior of the patty, resulting in a more complete kill throughout.

TABLE 4

| Ground Meat | Bacterial Load (CFU/patty) | % Reduction in *E. coli* bacteria |
| --- | --- | --- |
| Loosely packed | $1.7 \times 10^7$ | >99.99% |
| Densely packed | $5.0 \times 10^7$ | 99.5% |

EXAMPLE 13

*Escherichia coli* ATCC (American Type Culture Collection) #26 was grown in Tryptic Soy Broth (Difco 0370-17-3) to a log phase activity with an optical density of 0.8 at 600 nm containing one billion colony forming units per ml of culture. The concentration was verified using plate counts on three separate dilutions.

Uniform dispersal of the bacteria was assured in densely packed meat by the following inoculation method. Chiliground sirloin purchased six hours before use and stored at 8° C. weighing two kilograms was placed in a pan and pressed down into an even sheet. Five holes were punched into the meat with a glass rod, and 0.1 ml of the bacterial culture was pipetted into each hole. The meat was then kneaded to disperse the bacteria evenly. This was repeated three more times, with at least a minute of vigorous kneading each time. Since the two ml of an inoculum with a culture concentration of $10^9$ cfu per ml was added to the meat, a concentration of one million cfu/gram was introduced into the meat.

The meat was then reground to a fine texture on a bench-mounted, hand-cranked sausage grinder and formed into patties by replacing the meat in the pan and cutting patties out with a piece of tubing to form positive control (i.e., added *E. coli* bacteria) patties. The negative control (i.e., no added bacteria) ground sirloin from the same source was ground first in the uncontaminated grinder to prevent its own contamination. The patties were prepared in duplicate and consisted of negative controls tested at 0 and 60 hours, positive controls tested at 0, 4, 24 and 60 hours, and test samples (i.e., patties exposed to a chlorine dioxide releasing film of the present invention) at 0, 4, 24 and 60 hours.

The patties were placed between either unmodified paper or the papers coated with a 2:2 chlorine dioxide releasing film (as described in Example 11) in 10 cm diameter plastic Petri dishes with covers. Two Petri dishes containing duplicate samples were then put in recloseable plastic bags and stored for the required time at 4° C. in a common refrigerator.

Two samples were taken from each patty, one from the upper surface, T, contacted either by the unmodified paper or by the test paper with the chlorine dioxide releasing film, or from the middle one third of the patty, M. Samples were obtained with angle tipped forceps by either pinching across the surface to obtain a small scraping of the meat, or by digging down and exposing the middle third thickness region. The forceps were sterilized between samples by dipping in isopropanol and flaming.

Ten ml sterile water blanks in screw capped test tubes were tared to zero on a sensitive electronic scale, and roughly one gram samples added to the tubes and the weights recorded. The tubes were then capped and shaken vigorously to disperse the meat and release the bacteria.

0.1 ml of the supernatant was plated onto Tryptic Soy Agar (Difco 0369-17-6) in duplicate and spread with a glass triangle on a turntable. The glass spreader was sterilized between platings with isopropanol and flamed. The viable bacterial content of the samples was visualized by inverting the plates after 24 hours incubation at 37° C.

Uninoculated negative controls showed the normal amount of bacteria commonly seen in ground sirloin with no substantial growth noted over 60 hours at 4° C. Inoculated positive controls showed large amounts of bacterial growth for all times with very minor differences between the top and middle samples. If the unmodified paper had an antimicrobial effect, it was minor.

When the colony counts of chlorine dioxide exposed test samples were compared, a 50–100× kill was noted for the surface sample as compared to the interior test sample and the positive control samples, except for the reduced surface kill on the sample contacted with the weakly releasing film. As for the four hour exposed test samples, surface colony growth was 50–100× less than the interior test sample or the positive controls. The surprising observation made on the 60 hour sample was the high kill in both the interior and surface sections of the exposed samples when compared to the positive control samples.

Because the positive control plates were expected to be overloaded, a direct comparison for quantitation purposes was not accurate, although a rough count revealed anywhere between 50–200 fold reduction in colony count. As an alternative the test plate counts were compared to the confirmed inoculum titer instead.

A rough comparison may be made between the Ccfu and the inoculum figure (corrected for sampling dilution). This is termed the ratio to inoculum (RTI), which is intended to compare the viability of the treated sample and the maximum possible cfu count. RTI's were calculated for the 60 hour plates on the basis of the Ccfu count.

The average RTI for the top samples of the plates for the patties that were exposed to chlorine dioxide and tested for 60 hours was roughly 170, which would represent a 170 fold decrease in viability. The average RTI for the interior of these patties was roughly 50.

At 60 hours, however, large reductions in the bacterial viability in the center of the patty were seen. Cooking the patties that were exposed to chlorine dioxide and tested for 60 hours yielded a normal looking hamburger with no unusual odors being noted.

EXAMPLE 14

Loosely packed 0.75 inch thick, ground sirloin patties with approximately 25 cm$^2$ top surface area were formed by hand immediately after mixing and grinding in of *E. coli* ATCC #26 broth ($10^5$–$10^6$ cfu/gram). The initial inoculum was grown up to a slightly lesser extent than the inoculum used in Example 13. The loose packing was employed to help the penetration of chlorine dioxide through interconnected air passages.

The patties then were placed between either 2:4 or 3:6 chlorine dioxide releasing papers as described in Example 11, and covered with a Petri dish cover that was enclosed in a recloseable plastic bag. The samples were then stored at 4° C. for 3.5 days. After this exposure time the meat in contact with the 3:6 papers showed no bacterial growth from either a surface or interior sample when plated as described in Example 13. The interior of the patty exposed to the lower chlorine dioxide concentration (2:4) showed no bacterial growth from either surface or middle samples when plated.

When compared to the results of Example 13, these results confirm the deep penetrating biocidal action of chlorine dioxide when released in a controlled fashion over 2.5–3 days at 4° C. Clearly, the biocidal action is more effective for a porous meat structure.

An additional experiment using chicken breasts was also performed. A filet of chicken breast was repeatedly dipped in undiluted *E. coli* ATCC #6 broth ($10^8$–$10^9$ cfu/ml), placed between 2:2 chlorine dioxide releasing films and then closed inside a Petri dish that was placed in a recloseable plastic bag and placed in a refrigerator at 4° C. for 3.5 days. The surface of the meat was then swabbed and plated to get an indication of bacteria kill. Again no bacterial growth was noted after incubation.

EXAMPLE 15

Design of a chlorine dioxide releasing film suitable for controlled release and biocidal action within a container is described herein. The equation describing the concentration of chlorine dioxide in a coating of thickness, l, (0<x<l) which is covering the inside of a permeable container of total thickness l+a, where 'a' is the gas space thickness (l<x<l+a), above the coating is shown below. Chlorine dioxide is generated by means of a completely permeable thin film of infinitesimal thickness that lies on top of the coating at x=l.

$$C(x,t) = \sum_{n=0}^{\infty} \frac{Q\alpha_n^2 e^{-bt}\cos(\alpha_n x) \int_0^t e^{b\lambda} e^{-s\lambda} d\lambda}{[l(h-k'\alpha_n^2)^2 + (l+k')\alpha_n^2 + h]\cos(\alpha_n l)}$$

where, $b = D^c\alpha_n^2,\ k' = 4l/P,\ h = D^g/(lD^c)$

The terms, $\alpha_n$, in the infinite series above are roots of the equation:

$\alpha \tan (\alpha l) = h - k'\alpha^2$ $D^c$=Diffusion constant of chlorine dioxide (cm$^2$/sec) in coating $D^g$=Diffusion constant of chlorine dioxide (cm$^2$/sec) in gas phase l=Phenomenological length (cm) of leakage pore P=$C_{coat}(x=l)/C_{gas}(x=l)$=Henry's law constant for partition of the chlorine dioxide between the coating and the gas phase Q=chlorine dioxide generation constant from controlled release film (mole/cm$^2$/sec$^2$)

k=a, the total thickness of the gas layer s=inverse of the time of maximum release rate of chlorine dioxide from the controlled release film C(x,t) is evaluated for a given set of diffusion constants, leakage rate, h, phase partitioning and dimensional constant, k' chlorine dioxide release rate, Q, and inverse relaxation time for release, s, by plotting C($\alpha$) vs $\alpha$ at t=s$^{-1}$. As an example, C(l,t) is calculated for a Petri dish of 62 cm$^2$ cross-sectional area of 1 cm total thickness which includes 0.8 cm gas space and 0.2 cm Agar. Since the biologicals are introduced at x=l and grow in the Agar it is important to calculate this concentration. This calculation is necessitated by the strong partitioning of chlorine dioxide into the liquid phase once it is generated by the controlled release film. At the release rates generated by a test film the gas phase concentration was so low (<0.1 ppm) it could not be measured by the detector.

In order to complete the calculation Q, s, P, $D^g$, $D^c$ and l must be assigned or measured. Since Agar is 90% water it is assumed that P=40 can be used [J. J. Kaczur and D. W. Cawlfield, Kirk-Othmer Encycl. Chem. Tech. (4th Ed.), 5, 971 (1993)]. $D^c$=1.5×10$^{-5}$ cm$^2$/sec and $D^g$=0.12 cm$^2$/sec are reported in the Handbook of Chem. and Phys., 52nd Ed., F47 (1971). In actuality $D^g$ appears in the model only in conjunction with l since for the purposes of the calculation $C^g$ is assumed to be uniform in l<x<l+a.

The leakage flux constant, $D^g/l$, is evaluated by injecting a small quantity (about 10 ppm) of chlorine dioxide into the Petri dish containing no Agar and measuring the chlorine dioxide concentration as a function of time. The Petri dish employed will leak relatively rapidly because of the serrated edges of the bottom dish that is employed to assure good gas exchange necessary for biological growth.

($D^g/l$)=0.154 cm/sec

When the source function of the form Qte$^{-bt}$ is integrated from 0 to infinite time, $$\int_0^\infty Qte^{-bt}dt = Q/b^2 = \text{total moles of chlorine dioxide available}$$

For the purposes of the calculation the controlled release film of density 0.8 gram/cm$^3$ and total volume 0.315 cm$^3$ contains 15 wt. % sodium chlorite of molecular weight 90.44 g mole or 3.35×10$^4$ mole available chlorine dioxide (assuming complete reaction of 5 moles of ClO$_2^{-1}$ to 4 moles chlorine dioxide) and shows a maximum release rate at one day or s$^{-1}$=86,400 sec. This release maximum is typical of an acid releasing film separated from the chlorite containing film by an intermediate wax layer.

Q is thus calculated as 7.23×10$^{-16}$ mole/cm$^2$/sec$^2$ over a 62 cm$^2$ base area Petri dish where the area release rate is assumed to have no lateral dependence over the entire surface of the dish. This is a valid assumption since, even though the controlled release patch occupies a smaller area than the total cross-sectional area of the dish, both the gas and Agar diffusion rates of the chlorine dioxide are large in comparison to the time scale of the release rate.

Figure 10:
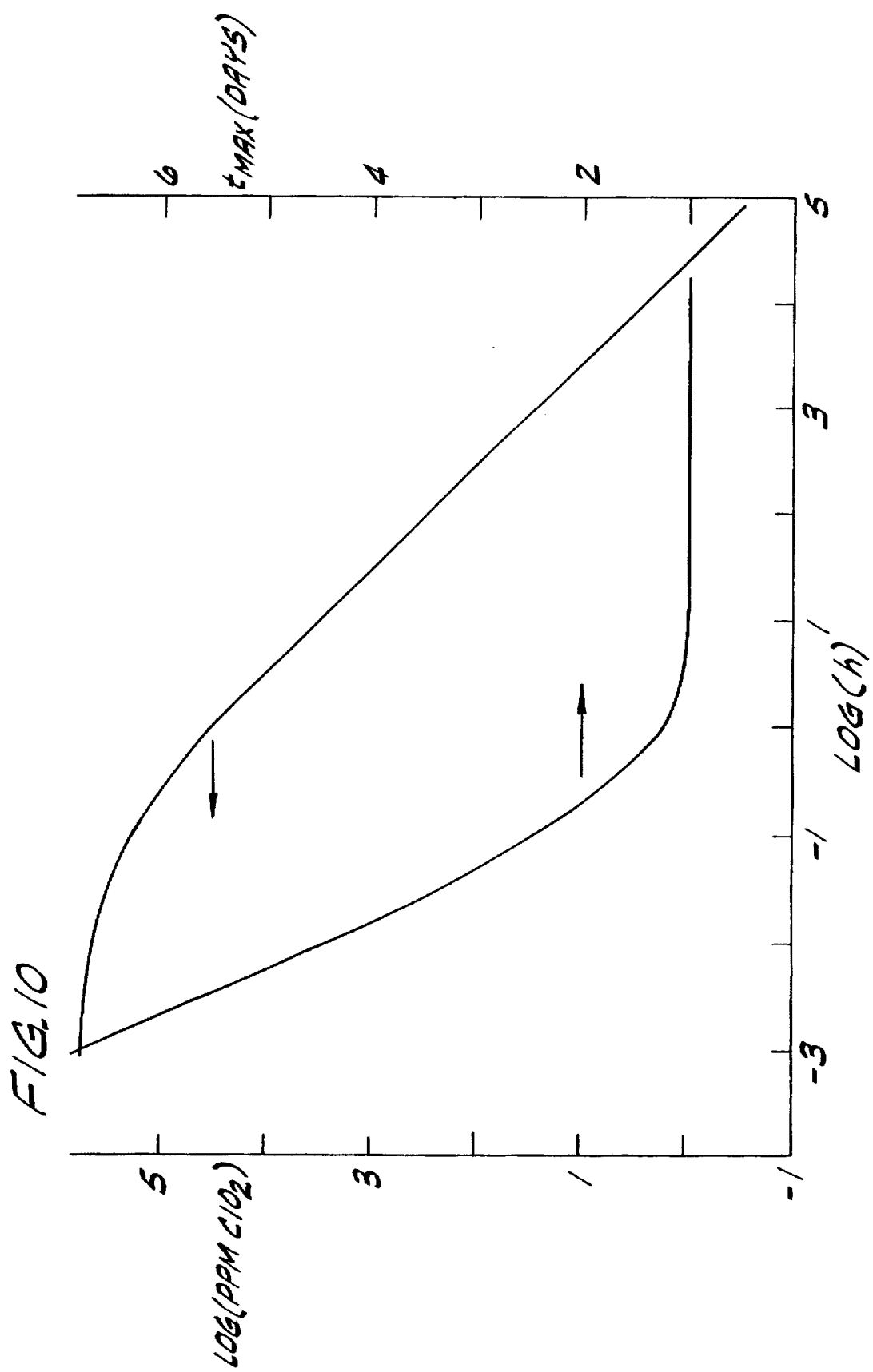
FIG. 10 is a plot of maximum chlorine dioxide concentration as a function of leakage from a container.

The concentration in the gel phase C(1,t) as a function of time is then calculated for a range of leakage rates, h as shown in FIG. 10. At fast leakage rates ($10^5 < h < 10^{-1}$ cm$^{-1}$), the release rate maximizes at t=s$^{-1}$ and the maximum concentration is proportional to h. In essence the concentration at any time significantly greater than the half time for leakage is simply some constant factor multiplied times the source generation rate. However as the leakage rate decreases $10^{-1} < h < 10^{-5}$, the maximum concentration is generated only at considerably longer time. Of course at h=0, no leakage occurs, the maximum concentration is approached asymptotically, and a total of $3.36 \times 10^{-4}$ moles chlorine dioxide (e.g. $Qs^{-2} \times 62$ cm$^2$) is distributed between the 0.2 cm thick gel phase and the 0.8 cm thick gas phase.

For the purposes of estimating how closely the h=0 concentration is approached at h=$8.31 \times 10^{-4}$ cm$^{-1}$, the concentration in the gel phase at t=$6.0 \times 10^5$ sec, x=1 ($2.4 \times 10^{-5}$ mole/cm$^3$) is used to calculate the total amount of chlorine dioxide in the Petri dish.

[0.8 cm(62 cm$^2$)1/40)+(0.2 cm)(62 cm$^2$)]($2.4 \times 10^{-5}$ mole/cm$^3$)= $3.27 \times 10^{-4}$ mole This value is very close to that expected for h=0.

For the leakage rate measured for the Petri dish in which the biological growth experiments are carried out, a maximum concentration of 2.5 ppm is expected in the gel phase at x=1 with a concentration of 0.06 ppm in the gas phase. About 0.25 ppm is required to kill mold spores.

A slightly more complicated environment would be a box of the same dimension as the Petri dish but with its gas space filed with absorbing particles packed with a volume fraction, $\epsilon$=0.5 cm$^3$/cm$^3$. The diffusion of gas through such a composite media has been studied [R. M. Barter and D. M. Grove, Trans. Far. Soc., 47, 826, 837 (1951); R. Ash and D. M. Grove, Trans. Far. Soc., 56, 1357 (1960)].

The diffusion constant $D^g$ of a gas flowing through a porous media must be replaced by:

$$D^g_p = D^g/[1+(2K_s/r)]$$

where $K_s$=Surface Henry's law coefficient in the relationship $$C_s' = K_s C^g$$

where $C_s'$ is the number of moles of gas absorbed/cm$^2$ of surface and $C^g$ is the gas phase concentration in mole/cm$^3$, r is the equivalent pore radius for a set of axially directed capillaries within a solid having porosity e and internal surface, A (cm$^2$/cm$^3$), r=2$\epsilon$/A.

For the purposes of the calculation of surface concentration of chlorine dioxide within the porous media, the particles are considered to be small enough so that the concentration of chlorine dioxide throughout the particles' thickness is equilibrated with the gas concentration. For the purposes of this calculation, the entire particle concentration is concentrated in the particle surface.

In this case the surface Henry's law coefficient is related to the bulk coefficient, $K_p$, by $$C^g(1-\epsilon)/A = C_s' = [(1-\epsilon)/A] K_p C^g$$

$$K_s = (1-\epsilon)K_p/A$$

$$D^g_p = D^g/[1+(1-\epsilon)K_p]$$

At a porosity of 0.5 and a partition coefficient of 40 into the particles, the diffusion constant for flow through the absorbing porous media would be reduced by a factor of 0.0244. This substantial reduction of apparent gas phase diffusion constant proportionally reduces the leakage rate, h, resulting in a proportional increase in the concentration expected at any time.

The amount, placement and controlled release characteristics required for a biocidal film are estimated where the film is protecting a small 62 cm$^3$ particle filled box that is assumed to leak at the same rate as the Petri dish, h=$8.3 \times 10^3$ cm$^{-1}$ (a rather good assumption for a typical loosely sealed box). A pallet of well packed, folded (unpacked) boxes might be an analogous case. Since mold spore kill is guaranteed at an exposure of 1 ppm chlorine dioxide for a few minutes, any strategy must generate at least this concentration in a pulsed release in moist regions of the box preferably after several days delay. Destruction of growing mold requires only 0.1–0.5 ppm for a few minutes. The destruction of the growth mechanisms of the cell is so complete that strains with a natural immunity to chlorine dioxide cannot develop. Conveniently, these concentrations are below the human olfactory detection limit of about 10 ppm.

Practically, since such a short exposure is required, a film that released chlorine dioxide in a pulsed fashion would be the ideal system. Of course, depending on the storage environment, this behavior would assure that the initial mold spore infection (originating inside and outside the box) and any subsequent infections (originating outside the box) were destroyed before any growth could occur. A continuous release of 1 ppm thus wastes about 98% of the available chlorite. The preparation of such a film is discussed in Example 16.

FIG. 11 shows the release characteristics expected for a controlled release film with a maximum release at 10 days, $3.35\times10^{-4}$ mole available chlorine dioxide (0.33 $cm^3$ film, 15% wt. % sodium chlorite), placed in a 0.5 porosity box with a bulk Henry's law coefficient of 40 vs air leaking with $h=202.76$ $cm^{-1}$.

A maximum concentration of 10.4 ppm is reached after 10 days and at least 1 ppm is generated for 0.4 day<t<46 days. Approximately 0.31 $cm^3$ of controlled release material is needed for this purpose. At a materials cost of $1.00/lb, the controlled release material cost required to do the job would be about 0.056 cents. Thus, a box containing 1.1 liters of material could be protected for 1 cent with the above listed parameters.

EXAMPLE 16

The pulsed release capabilities of a multiple layered composite can be calculated as follows to determine whether the composite will provide the desired sustained release rates for a particular application. The time required for complete cation exchange can be predicted from the mobile ion concentration in each layer, $C_i$, wherein i is A, B, or C. In order to determine such a time period, hydronium ion transport across the intermediate layer C is considered to be the rate controlling step, and the diffusion constant and effective mobile ion concentration for hydrogen ion are considered the same in layers A, B and C. Chlorite ion is considered to be relatively immobile and the reaction of chlorite to chlorine dioxide is considered to occur instantaneously once a hydrogen ion enters the hydrophilic layer B.

Hydronium ion mobility in intermediate layer C can be estimated by using experimental data reported by J. L. Crowley et al., J. Poly. Sc., Poly. Phys. Ed., 14, 1769 (1976). Crowley et al. studied the ionic mobility in a graft copolymer of low density polyethylene (79 wt. %) and sulfonated polystyrene (21 wt. %) as a function of ion type, water content and temperature. Sodium, potassium and silver ions travel along polymer bound sulfonate groups by exchange with hydronium cations. At high water contents of 3–6 wt. % phase separation of ion clusters in a hydrophobic matrix is likely. The reported silver ion mobility and mobile ion concentration is quite high under these conditions ($\mu=3.0\times 10^{-4}$ cm$^2$/StatV-sec, C=$3.3\times 10^{-4}$ mol/cc). However, in "dry" films both the mobility and mobile ion concentration decrease substantially ($\mu=1.4\times 10^{-4}$ cm$^2$/StatV-sec, C=$8.3\times 10^{-7}$ mol/cc). The ion diffusion constant D can be calculated from the reported ion mobility using the equation D=(kT$\mu$)/q, where k is Boltzman's constant, T is the absolute temperature, $\mu$ is ion mobility and q is electron charge. The calculated ion diffusion constants are $1.21\times 10^{-8}$ cm$^2$/sec and $2.58\times 10^{-8}$ cm$^2$/sec for a dry and wet (6 wt. % water) silver counterion loaded film, respectively.

The morphology of such a copolymer would be very similar to the two material system of the present invention in that both include partially connected ion clusters localized at spherulite boundaries within the hydrophobic layer.

The total amount of hydronium ion that has diffused across boundary AC (moles/cm$^2$) in time t is represented by the function Q:

$$Q(t)/lC_A = (Dt/l^2) - 1/6 - 2(\pi)^{-2} \sum_{n=1}^{\infty} (-1)^n n^{-2} \exp(-Dn^2\pi^2 t/l^2)$$

Breakthrough of hydronium ion into hydrophilic layer B will occur at $(Dt/l^2)=0.1$ (t=10.4 min, l=5 mil or $1.27\times 10^{-2}$ cm) and steady state diffusion is reached at $(Dt/l^2)=0.45$ (t=46.9 min, l=5 mil). The first two terms in the above equation dominate after steady state is reached. Thus under "wet" conditions (6 wt % water), $Q(t)=lC_A [(Dt/l^2)-1/6]=5.72\times 10^{-5}$ mole/day-cm$^2$ at 5 mil thickness. The hydronium ion in a 1 cm$^2$ area film and $1.27\times 10^{-2}$ cm thickness ($1.65\times 10^{-5}$ mole hydronium ion initially) should be almost completely reacted in the chlorite layer in 7 hours. In the "dry" film, which is typical of polyethylene contaminated with ions, $Q(t)=DtC_A/l=6.83\times 10^{-8}$ mole/day-cm$^2$ at 5 mil thickness. Because of the much lower mobile ion concentration, 247 days are required for the hydronium ion to completely diffuse into the hydrophilic layer B. Thus, a multiple layered composite providing from about one day to about 247 days of chlorine dioxide release can be formulated using the two layered composites of the present invention.

The chlorine dioxide release rate is generally rapid when chlorine dioxide release is initiated in a composite containing an intermediate layer because chlorine decomposition is a function of pH. A minimum concentration of hydronium ion is transferred before chlorite decomposition into chlorine dioxide occurs due to the buffering action of the hydrophilic layer containing the chlorite.

The effect of viscosity on reaction rate, the rate of hydration of the film required to produce the minimal amount of free water necessary for catalysis of chlorine dioxide production, and the changing mobile ion concentration and diffusion constant supported by the A, B and C layers can affect hydronium ion transport.

An amount of water must be present in intermediate layer C for transport of hydronium ion. Water is transported through a hydrocarbon matrix as single molecules, except at higher water activities where some tendency to form clusters is noticed. The permeation rate of water through a 5 mil thick high density polyethylene film of 1 cm$^2$ face area would be $6.89\times 10^{-6}$ mole/day/cm$^2$/5mil (90% RH, 38° C.) as reported by Wessling et al., Encycl. Poly. Sci. Eng., 17, 510 (1989). This permeation rate is significantly less than that seen for polyethylene ionomers which typically contain $3.35\times 10^{-4}$ mole/cc ionic groups at a minimum ($4.08\times 10^{-5}$ mole/day/cm$^2$/5 mil) [Zutty et al., Encycl. Poly. Sci. Tech., 6, 425 (1967)]. The latter ionic content is suitable for layers A, B and C, each of which has the potential to absorb $3.3\times 10^{-4}$ mole/cc$\times 10$ moles of water (assuming 10 H$_2$O/H$_3$O$^+$ ion) or $4.2\times 10^{-5}$ mole water/cm$^2$/5 mil (6 wt % water). Therefore, 5 mil A and B layers would require about 1 day to saturate to 6% water from an initially dry state. At most, an additional day would then be required to saturate the intermediate layer C.

While the invention is susceptible to various modifications and alternative forms, specific embodiments thereof have been shown by way of example in the drawings and have been described herein in detail. It should be understood, however, that it is not intended to limit the invention to the particular form disclosed, but on the contrary, the intention is to cover all modifications, equivalents and alternatives falling within the spirit and scope of the invention as defined by the appended claims.

We claim:

1. A multilayered composite for providing sustained release of chlorine dioxide comprising:
   a hydrophobic layer containing an acid releasing agent; and
   a hydrophilic layer containing chlorite anions, the hydrophilic and hydrophobic layers being adjacent and substantially free of water, the hydrophilic layer being capable of releasing chlorine dioxide upon hydrolysis of the acid releasing agent.

2. The composite of claim 1 wherein a surface of the hydrophilic layer and a surface of the hydrophobic layer are in contact, and the hydrolysis and chlorine dioxide release occur after contact of the surfaces is made.

3. The composite of claim 1 further including an intermediate layer between the hydrophilic layer and the hydrophobic layer to control diffusion of water into the hydrophobic layer or the diffusion of hydronium ions produced from the hydrolysis into the hydrophilic layer, so as to control the rate of chlorine dioxide release.

4. The composite of claim 2 further including a moisture regulating layer in contact with a second surface of the hydrophobic layer to control the rate of moisture ingress into the hydrophobic layer.

5. The composite of claim 3 further including a moisture regulating layer in contact with a surface of the hydrophobic layer to control the rate of moisture ingress into the hydrophobic layer.

6. The composite of claim 2 further including a first moisture regulating layer in contact with a second surface of the hydrophobic layer and a second moisture regulating layer in contact with a second surface of the hydrophilic layer to control the rate of moisture ingress into the hydrophobic layer.

7. The composite of claim 3 further including a first moisture regulating layer in contact with a surface of the hydrophobic layer and a second moisture regulating layer in contact with a surface of the hydrophilic layer to control the rate of moisture ingress into the hydrophobic layer.

8. The composite of claim 3 wherein the intermediate layer comprises a sulfonated or phosphorylated oligoalkene or polyalkene polyionomer, a lipid substituted polyhydroxy alcohol phosphate or phosphosilicate, or a mixture of a lipid substituted polyhydroxy alcohol phosphate or phosphosilicate with an alkene polymer or oligomer; the hydrophilic layer further comprises an amide, an amine, glycerin, acetonitrile, ethylene glycol, or an alcohol; the hydrophobic layer further comprises atactic polypropylene, hydrocarbon wax, chlorinated wax, or polyethylene wax; and the acid releasing agent includes a carboxylic acid, an ester, an anhydride, an acyl halide, phosphoric acid, a phosphate ester, a trimethylsilyl phosphate ester, a dialkyl phosphate, sulfonic acid, a sulfonic acid ester, a sulfonic acid chloride, or a phosphosilane of a glycerol based ester.

9. The composite of claim 3 wherein the hydrophilic layer, the hydrophobic layer, or the intermediate layer contain an anhydrous salt or a desiccant to delay the hydrolysis.

10. A multilayered composite for providing sustained release of chlorine dioxide comprising:

a layer comprising a hydrophobic phase containing an acid releasing agent and a hydrophilic phase containing chlorite anions, the hydrophilic and hydrophobic phases being interdispersed and substantially free of water; and a moisture regulating layer in contact with a surface of the layer, such that moisture permeating the moisture regulating layer hydrolyzes the acid releasing agent to initiate release of chlorine dioxide from the multilayered composite.

11. The composite of claim 10 wherein a second surface of the layer is in contact with a second moisture regulating layer.

12. The composite of claim 10 wherein the layer is a dispersion having a phase size of between about 0.2 microns and about 100 microns.

13. The composite of claim 10 wherein the hydrophilic phase further comprises an amide, an amine, glycerin, acetonitrile, ethylene glycol, or an alcohol; the hydrophobic phase further comprises atactic polypropylene, hydrocarbon wax, chlorinated wax, or polyethylene wax; and the acid releasing agent includes a carboxylic acid, an ester, an anhydride, an acyl halide, phosphoric acid, a phosphate ester, a trimethylsilyl phosphate ester, a dialkyl phosphate, sulfonic acid, a sulfonic acid ester, a sulfonic acid chloride, or a phosphosilane of a glycerol based ester.

14. The composite of claim 10 wherein the layer contains an anhydrous salt or a desiccant to delay the hydrolysis.

15. A multilayered composite for providing time pulsed release of chlorine dioxide comprising:

at least one hydrophobic layer containing an acid releasing agent, at least one hydrophilic layer containing chlorite anions, and at least three barrier layers to control the diffusion of water into the hydrophobic layer or the diffusion of hydronium ions produced by hydrolysis of the acid releasing agent into the hydrophilic layer, the arrangement of the layers in the composite being defined by the formula $C(ACB)_nC$ wherein C is a barrier layer, A is a hydrophobic layer, B is a hydrophilic layer, and n is an integer ranging from 1 to 10.

16. The composite of claim 15 wherein the barrier layers independently comprise a sulfonated or phosphorylated oligoalkene or polyalkene polyionomer, a lipid substituted polyhydroxy alcohol phosphate or phosphosilicate, or a mixture of a lipid substituted polyhydroxy alcohol phosphate or phosphosilicate with an alkene polymer or oligomer; the hydrophilic layer further comprises an amide, an amine, glycerin, acetonitrile, ethylene glycol, or an alcohol; the hydrophobic layer further comprises atactic polypropylene, hydrocarbon wax, chlorinated wax, or polyethylene wax; and the acid releasing agent includes a carboxylic acid, an ester, an anhydride, an acyl halide, phosphoric acid, a phosphate ester, a trimethylsilyl phosphate ester, a dialkyl phosphate, sulfonic acid, a sulfonic acid ester, a sulfonic acid chloride, or a phosphosilane of a glycerol based ester.

17. The composite of claim 15 wherein the hydrophilic layer, the hydrophobic layer, or the barrier layers contain an anhydrous salt or a desiccant to delay the hydrolysis.

18. The composite of claim 8 wherein the amide of the hydrophilic layer is selected from the group consisting of formamide, acrylamide-isopropylacrylamide, a copolymer of formamide and acrylamide-isopropylacrylamide, and a copolymer of acrylamide, isopropylacrylamide or N,N-methylene bisacrylamide and a primary amine or a secondary amine.

19. The composite of claim 8 wherein the alcohol of the hydrophilic layer is selected from the group consisting of methanol, ethanol, methoxyethanol or ethoxyethanol.

20. The composite of claim 8 wherein the amine of the hydrophilic layer is selected from the group consisting of a primary amine, a secondary amine, a tertiary amine having pendant hydrogen bonding groups, and a tertiary amine having non-hydrogen bonding pendant groups dissolved in a hydrophilic solvent.

21. The composite of claim 8 wherein the amine of the hydrophilic layer is selected from monoethanolamine, diethanolamine, triethanolamine, a copolymer of 1,3-diaminopropane or 1,2-diaminoethane and N,N-methylene bisacrylamide, 4-dimethylaminopyridine, tetramethylene ethylene diamine, N,N-dimethylamino cyclohexane, 1-(N-dipropylamino)-2-carboxyamido ethane and 1-(N-dimethylamino)-2-carboxyamido ethane.

22. The composite of claim 8 wherein the hydrophilic layer includes an iminium chlorite.

23. The composite of claim 8 wherein the hydrophilic layer includes an amine having the formula $R_{3-x}NH_x$; $R_1R_2NCH_2CH_2C(O)NH_2$; solubilized $N(CH_2CH_2OH)_{3-x}H_x$, $R_3N(NCH_2CH_2C(O)NH_2)_2$, $(CH_3)_2N(CH_2)_zN(CH_3)_2$, $R_5R_6N(CH_2)_zNHC(O)NH_2$, $N(CH_2CH_2NHC(O)NH_2)_3$,

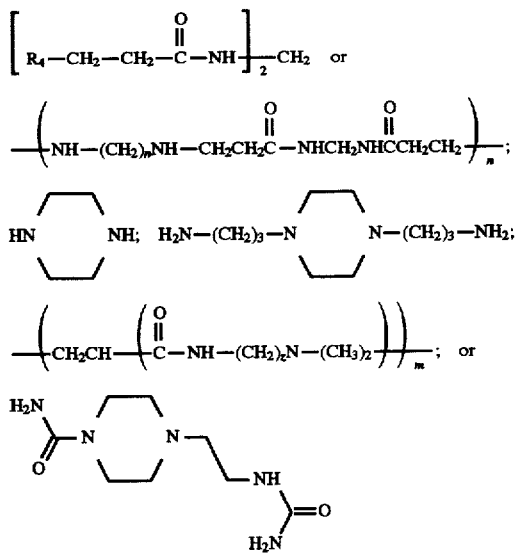

wherein: R substituents are, independently, —$(CH_2CH_2O)_y$H, —$C(CH_3)_2(CH_2)_zOH$, —$(CH_2)_zNH(CH_2CH_2O)_zH$, —$CH(CH_3)_2$,

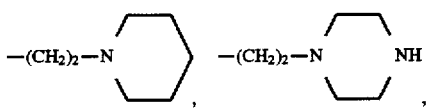

alkyl, cycloalkyl, benzyl, acrylamide, or pyridyl; $R_1$, $R_2$, $R_5$, and $R_6$ are alkyl; $R_3$ is straight chain $C_6$ to $C_{12}$ alkyl; $R_4$ is cycloalkyl or benzyl; m is 1–100; n is 2 or 3; x is 0, 1 or 2; y is 1 or 2; and z is 1–6.

24. The composite of claim 8 wherein the anhydride is selected from the group consisting of an organic acid anhydride, a mixed organic acid anhydride, a homopolymer of an organic acid anhydride or a mixed inorganic acid anhydride, and a copolymer of an organic acid anhydride or a mixed inorganic acid anhydride with a monomer containing a double bond.

25. The composite of claim 24 wherein the mixed inorganic acid anhydride contains a phosphorus-oxygen-silicon bond.

26. The composite of claim 8 wherein the anhydride is a copolymer of maleic anhydride, methacrylic anhydride, acetic anhydride, propionic anhydride, or succinic anhydride, and vinyl, styrene or an alkene.

27. The composite of claim 8 wherein the acid releasing agent is an anhydride or phosphate ester blended with or grafted to polypropylene, polyethylene or polystyrene.

28. The composite of claim 8 wherein the trimethylsilyl phosphate ester is $(CH_3)_3SiOP(O)(OR)_2$ wherein R is a non-hydrogen bonding group, alkyl or aryl.

29. The composite of claim 13 wherein the amide of the hydrophilic phase is selected from the group consisting of formamide, acrylamide-isopropylacrylamide, a copolymer of formamide and acrylamide-isopropylacrylamide, and a copolymer of acrylamide, isopropylacrylamide or N,N-methylene bisacrylamide and a primary amine or a secondary amine.

30. The composite of claim 13 wherein the alcohol of the hydrophilic phase is selected from the group consisting of methanol, ethanol, methoxyethanol or ethoxyethanol.

31. The composite of claim 13 wherein the amine of the hydrophilic phase is selected from the group consisting of a primary amine, a secondary amine, a tertiary amine having pendant hydrogen bonding groups, and a tertiary amine having non-hydrogen bonding pendant groups dissolved in a hydrophilic solvent.

32. The composite of claim 13 wherein the amine of the hydrophilic phase is selected from monoethanolamine, diethanolamine, triethanolamine, a copolymer of 1,3-diaminopropane or 1,2-diaminoethane and N,N-methylene bisacrylamide, 4-dimethylaminopyridine, tetramethylene ethylene diamine, N,N-dimethylamino cyclohexane, 1-(N-dipropylamino)-2-carboxyamido ethane and 1-(N-dimethylamino)-2-carboxyamido ethane.

33. The composite of claim 13 wherein the hydrophilic phase includes an iminium chlorite.

34. The composite of claim 13 wherein the hydrophilic phase includes an amine having the formula $R_{3-x}NH_x$; $R_1R_2NCH_2CH_2C(O)NH_2$; solubilized N $(CH_2CH_2OH)_{3-x}$ $H_x$, $R_3N(NCH_2CH_2C(O)NH_2)_2$, $(CH_3)_2N(CH_2)_zN(CH_3)_2$, $R_5R_6N(CH_2)_zNHC(O)NH_2$, $N(CH_2CH_2NHC(O)NH_2)_3$,

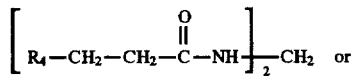

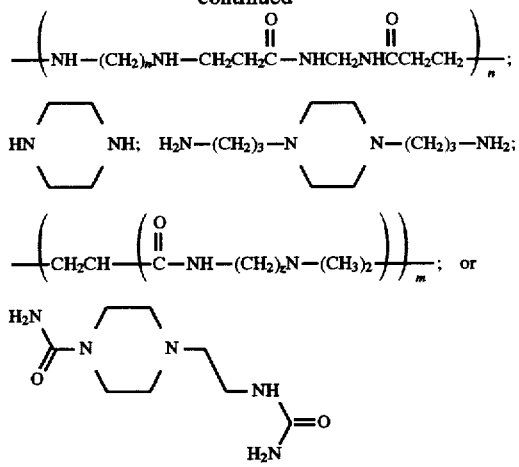

wherein: R substituents are, independently, $-(CH_2CH_2O)_y$H, $-C(CH_3)_2(CH_2)_zOH$, $-(CH_2)_zNH(CH_2CH_2O)_zH$, $-CH(CH_3)_2$,

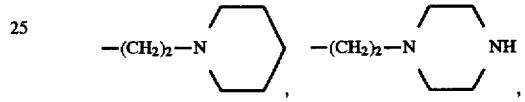

alkyl, cycloalkyl, benzyl, acrylamide, or pyridyl; $R_1$, $R_2$, $R_5$, and $R_6$ are alkyl; $R_3$ is straight chain $C_6$ to $C_{12}$ alkyl; $R_4$ is cycloalkyl or benzyl; m is 1–100; n is 2 or 3; x is 0, 1 or 2; y is 1 or 2; and z is 1–6.

35. The composite of claim 13 wherein the anhydride is selected from the group consisting of an organic acid anhydride, a mixed organic acid anhydride, a homopolymer of an organic acid anhydride or a mixed inorganic acid anhydride, and a copolymer of an organic acid anhydride or a mixed inorganic acid anhydride with a monomer containing a double bond.

36. The composite of claim 35 wherein the mixed inorganic acid anhydride contains a phosphorus-oxygen-silicon bond.

37. The composite of claim 13 wherein the anhydride is a copolymer of maleic anhydride, methacrylic anhydride, acetic anhydride, propionic anhydride, or succinic anhydride, and vinyl, styrene or an alkene.

38. The composite of claim 13 wherein the acid releasing agent is an anhydride or phosphate ester blended with or grafted to polypropylene, polyethylene or polystyrene.

39. The composite of claim 13 wherein the trimethylsilyl phosphate ester is $(CH_3)_3SiOP(O)(OR)_2$ wherein R is a non-hydrogen bonding group, alkyl or aryl.

40. The composite of claim 16 wherein the amide of the hydrophilic layer is selected from the group consisting of formamide, acrylamide-isopropylacrylamide, a copolymer of formamide and acrylamide-isopropylacrylamide, and a copolymer of acrylamide, isopropylacrylamide or N,N-methylene bisacrylamide and a primary amine or a secondary amine.

41. The composite of claim 16 wherein the alcohol of the hydrophilic layer is selected from the group consisting of methanol, ethanol, methoxyethanol or ethoxyethanol.

42. The composite of claim 16 wherein the amine of the hydrophilic layer is selected from the group consisting of a primary amine, a secondary amine, a tertiary amine having pendant hydrogen bonding groups, and a tertiary amine having non-hydrogen bonding pendant groups dissolved in a hydrophilic solvent.

43. The composite of claim 16 wherein the amine of the hydrophilic layer is selected from monoethanolamine, diethanolamine, triethanolamine, a copolymer of 1,3-diaminopropane or 1,2-diaminoethane and N,N-methylene bisacrylamide, 4-dimethylaminopyridine, tetramethylene ethylene diamine, N,N-dimethylamino cyclohexane, 1-(N-dipropylamino)-2-carboxyamido ethane and 1-(N-dimethylamino)-2-carboxyamido ethane.

44. The composite of claim 16 wherein the hydrophilic layer includes an iminium chlorite.

45. The composite of claim 16 wherein the hydrophilic layer includes an amine having the formula $R_{3-x}NH_x$; $R_1R_2NCH_2CH_2C(O)NH_2$; solubilized N $(CH_2CH_2OH)_{3-x}$ $H_x$, $R_3N(NCH_2CH_2C(O)NH_2)_2$, $(CH_3)_2N(CH_2)_zN(CH_3)_2$, $R_5R_6N(CH_2)_zNHC(O)NH_2$, $N(CH_2CH_2NHC(O)NH_2)_3$,

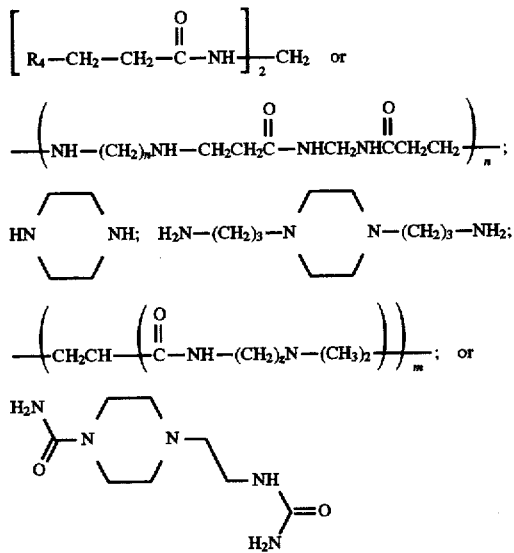

wherein: R substituents are, independently, —$(CH_2CH_2O)_y$H, —$C(CH_3)_2(CH_2)_zOH$, —$(CH_2)_zNH(CH_2CH_2O)_zH$, —$CH(CH_3)_2$,

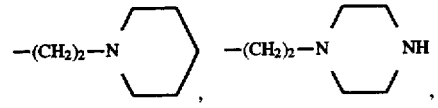

alkyl, cycloalkyl, benzyl, acrylamide, or pyridyl; $R_1$, $R_2$, $R_5$, and $R_6$ are alkyl; $R_3$ is straight chain $C_6$ to $C_{12}$ alkyl; $R_4$ is cycloalkyl or benzyl; m is 1–100; n is 2 or 3; x is 0, 1 or 2; y is 1 or 2; and z is 1–6.

46. The composite of claim 16 wherein the anhydride is selected from the group consisting of an organic acid anhydride, a mixed organic acid anhydride, a homopolymer of an organic acid anhydride or a mixed inorganic acid anhydride, and a copolymer of an organic acid anhydride or a mixed inorganic acid anhydride with a monomer containing a double bond.

47. The composite of claim 46 wherein the mixed inorganic acid anhydride contains a phosphorus-oxygen-silicon bond.

48. The composite of claim 16 wherein the anhydride is a copolymer of maleic anhydride, methacrylic anhydride, acetic anhydride, propionic anhydride, or succinic anhydride, and vinyl, styrene or an alkene.

49. The composite of claim 16 wherein the acid releasing agent is an anhydride or phosphate ester blended with or grafted to polypropylene, polyethylene or polystyrene.

50. The composite of claim 16 wherein the trimethylsilyl phosphate ester is $(CH_3)_3SiOP(O)(OR)_2$ wherein R is a non-hydrogen bonding group, alkyl or aryl.

* * * * *